(12) United States Patent
Yanagisawa

(10) Patent No.: US 10,031,554 B2
(45) Date of Patent: Jul. 24, 2018

(54) DISPLAY DEVICE, MODULE, DISPLAY SYSTEM, AND ELECTRONIC DEVICE

(71) Applicant: Semiconductor Energy Laboratory Co., Ltd., Atsugi-shi, Kanagawa-ken (JP)

(72) Inventor: Yuichi Yanagisawa, Kanagawa (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 168 days.

(21) Appl. No.: 14/947,084

(22) Filed: Nov. 20, 2015

(65) Prior Publication Data

US 2016/0154435 A1    Jun. 2, 2016

(30) Foreign Application Priority Data

Nov. 28, 2014 (JP) .................................. 2014-242112
Dec. 9, 2014 (JP) .................................. 2014-249194

(51) Int. Cl.

| | |
|---|---|
| *A61B 5/18* | (2006.01) |
| *G06F 1/16* | (2006.01) |
| *H04N 13/04* | (2006.01) |
| *A61B 3/113* | (2006.01) |
| *A61B 3/00* | (2006.01) |
| *H04N 13/00* | (2018.01) |

(52) U.S. Cl.
CPC ............ *G06F 1/1652* (2013.01); *A61B 3/005* (2013.01); *A61B 3/113* (2013.01); *A61B 5/18* (2013.01); *G06F 1/1622* (2013.01); *G06F 1/1624* (2013.01); *G06F 1/1643* (2013.01); *H04N 13/0033* (2013.01); *H04N 13/0409* (2013.01); *H04N 13/0484* (2013.01)

(58) Field of Classification Search
None
See application file for complete search history.

(56) References Cited

U.S. PATENT DOCUMENTS

| | | |
|---|---|---|
| 6,483,484 B1 | 11/2002 | Yamazaki et al. |
| 6,791,462 B2 | 9/2004 | Choi |
| 7,138,922 B2 | 11/2006 | Strumolo et al. |
| 7,598,927 B2 | 10/2009 | Yamazaki et al. |
| 8,890,187 B2 | 11/2014 | Arasawa |

(Continued)

FOREIGN PATENT DOCUMENTS

| | | |
|---|---|---|
| JP | 2011/238908 | 11/2011 |
| WO | WO-2004/003630 | 1/2004 |

*Primary Examiner* — Eileen M Adams
(74) *Attorney, Agent, or Firm* — Fish & Richardson P.C.

(57) ABSTRACT

A display device or a display system with which a viewer can feel a strong or natural stereoscopic effect in a two-dimensional image and is less likely to be fatigued is provided. The display system includes a display portion, a detection portion, and a control portion. The display portion is flexible. The detection portion is configured to detect the conditions of a viewer's eye to obtain detection information and to supply the detection information to the control portion. The control portion is configured to extract information on the viewer's fatigue from the detection information and to change the curvature of the display portion on the basis of the information on the viewer's fatigue. The central angle of the curved surface of the display portion is preferably greater than or equal to 20° and less than 90°.

19 Claims, 25 Drawing Sheets

(56) References Cited

U.S. PATENT DOCUMENTS

| | | |
|---|---|---|
| 9,111,841 B2 | 8/2015 | Yamazaki et al. |
| 2008/0224951 A1 | 9/2008 | Alberth |
| 2009/0121882 A1 | 5/2009 | Al-Mutairi |
| 2010/0164860 A1* | 7/2010 | Misono ............... F21V 5/00 |
| | | 345/102 |
| 2010/0295827 A1* | 11/2010 | Lim .................. G09G 3/20 |
| | | 345/204 |
| 2011/0134145 A1 | 6/2011 | Moriwaki |
| 2012/0075166 A1 | 3/2012 | Marti et al. |
| 2013/0011819 A1* | 1/2013 | Horseman ........... A61B 5/6887 |
| | | 434/257 |
| 2013/0016314 A1* | 1/2013 | Itou ................ G02F 1/133707 |
| | | 349/106 |
| 2013/0114193 A1 | 5/2013 | Joo et al. |
| 2013/0155655 A1 | 6/2013 | Lee et al. |
| 2013/0264549 A1 | 10/2013 | Yamazaki et al. |
| 2013/0300313 A1 | 11/2013 | Yamazaki et al. |
| 2014/0081117 A1* | 3/2014 | Kato ................ A61B 5/0496 |
| | | 600/383 |
| 2014/0118319 A1 | 5/2014 | Jeon |
| 2015/0109201 A1 | 4/2015 | Yamazaki et al. |
| 2015/0145755 A1 | 5/2015 | Yamazaki et al. |
| 2015/0146352 A1 | 5/2015 | Yanagisawa et al. |
| 2015/0177789 A1 | 6/2015 | Jinbo |
| 2015/0215601 A1* | 7/2015 | Zhou ................ H04N 13/042 |
| | | 348/43 |
| 2015/0301636 A1 | 10/2015 | Akimoto et al. |
| 2015/0316958 A1 | 11/2015 | Takesue |
| 2016/0118616 A1 | 4/2016 | Hiroki et al. |

* cited by examiner

FIG. 1A1
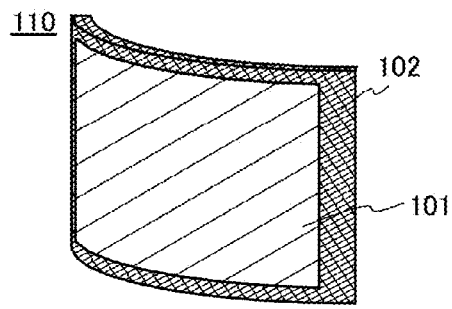
FIG. 1B1
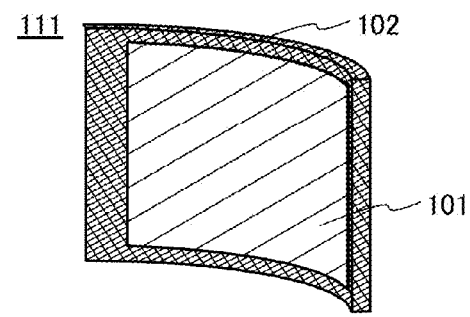
FIG. 1A2
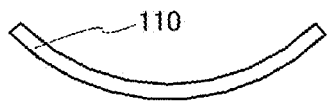
FIG. 1B2
FIG. 1C1
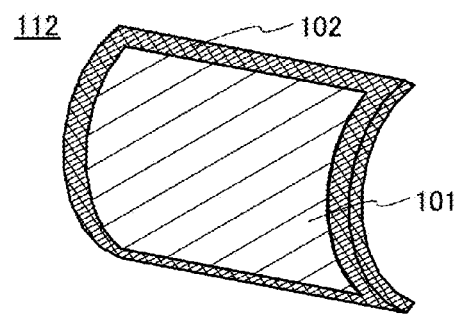
FIG. 1D1
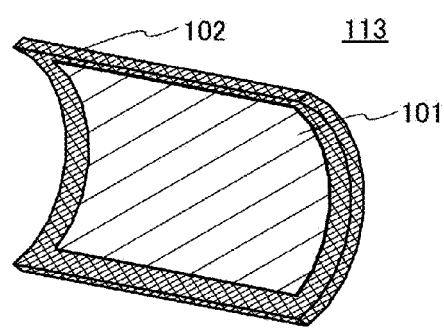
FIG. 1C2
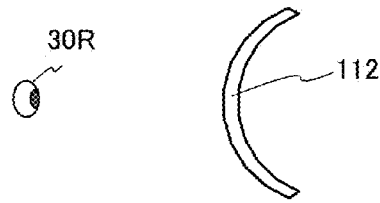
FIG. 1D2
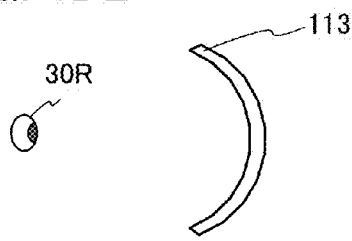

FIG. 3A1
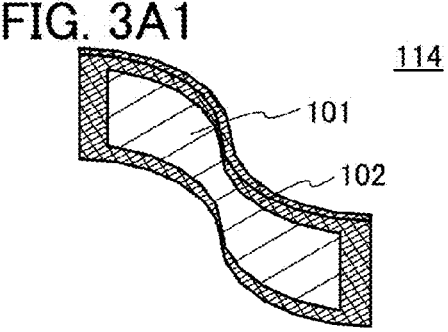
FIG. 3A2
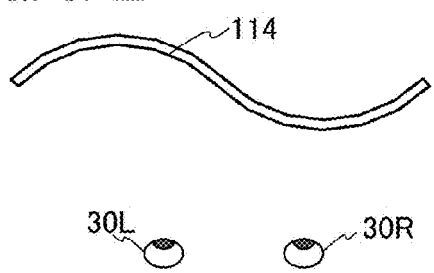
FIG. 3B
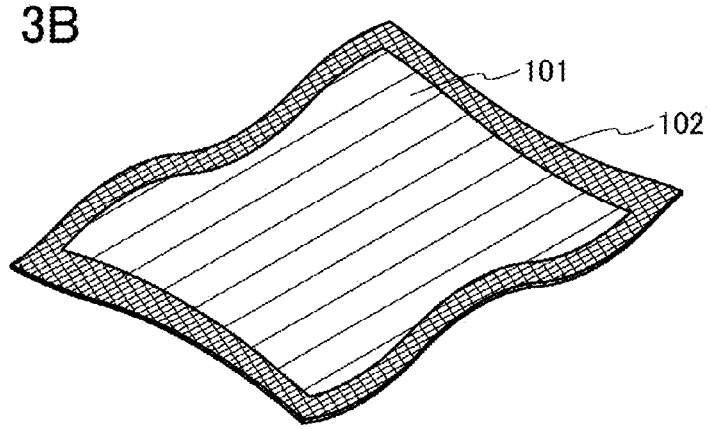

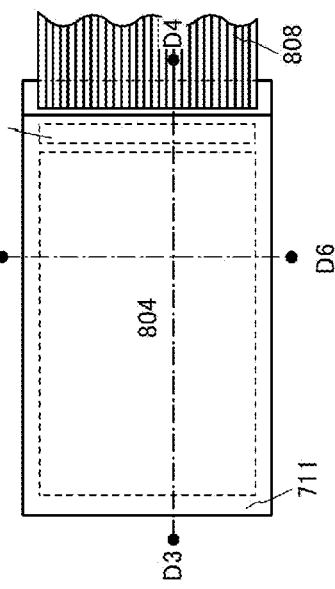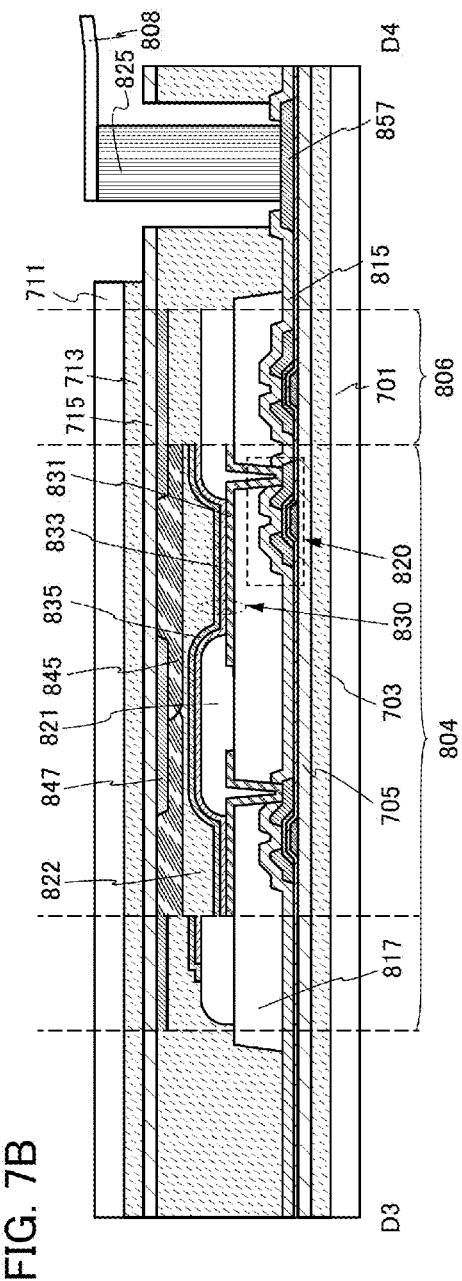

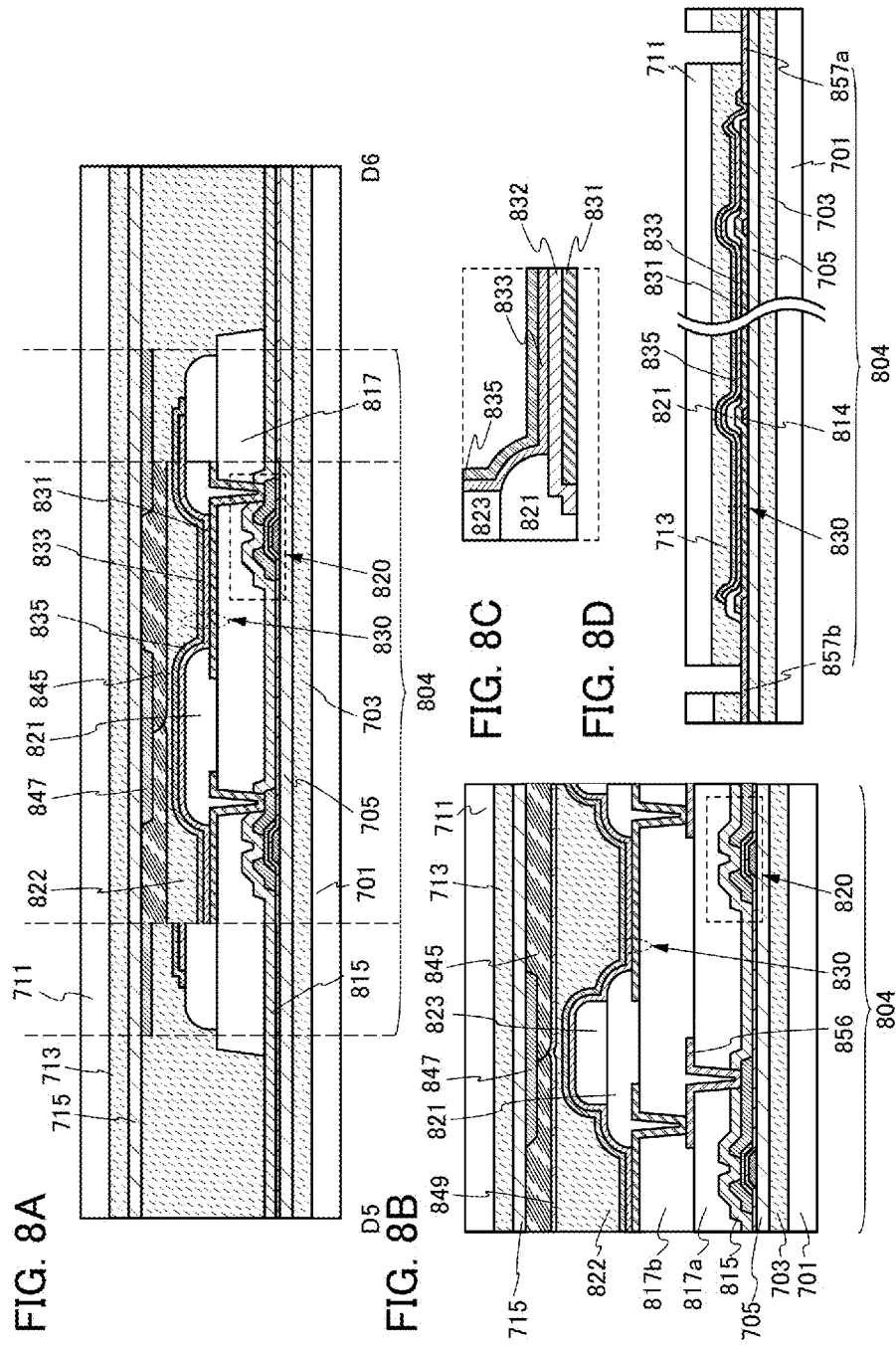

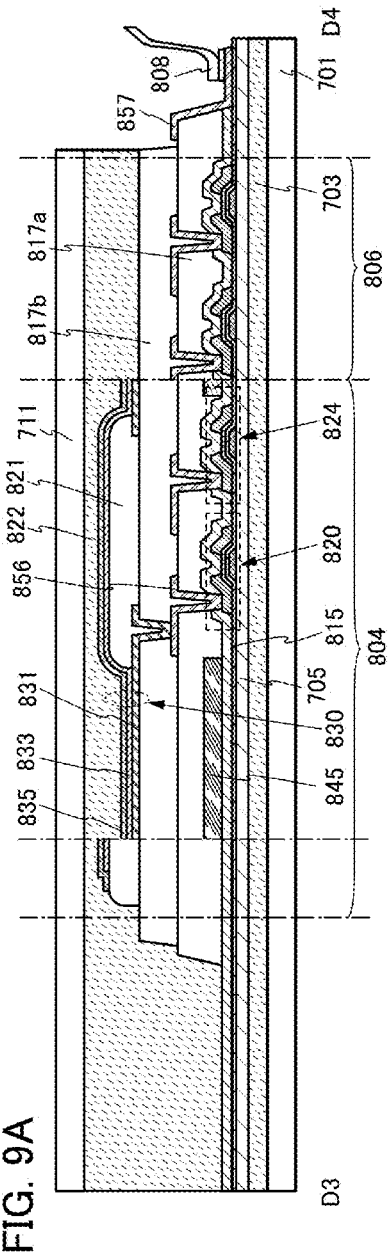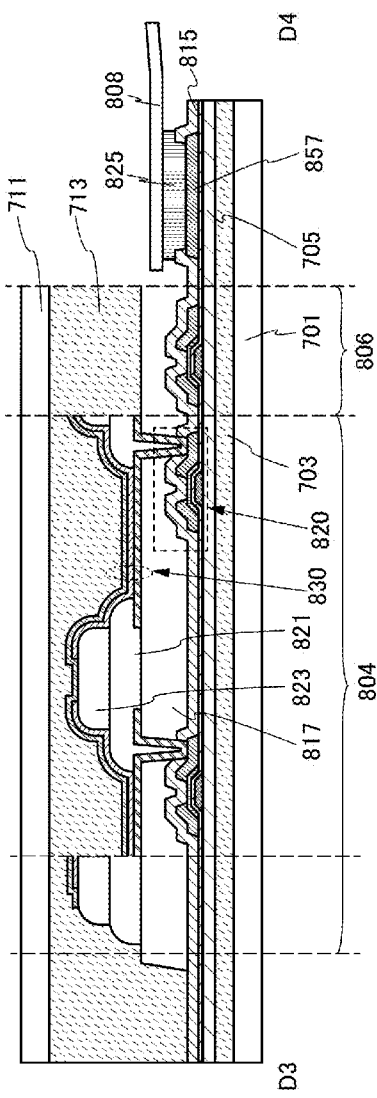

FIG. 14A
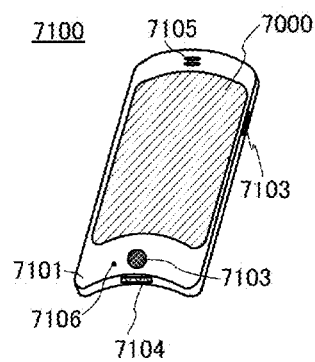
FIG. 14B
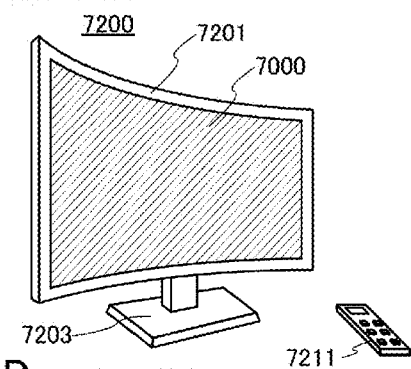
FIG. 14C1
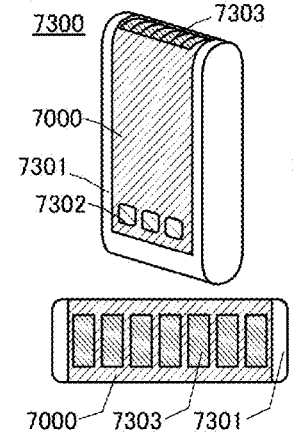
FIG. 14D
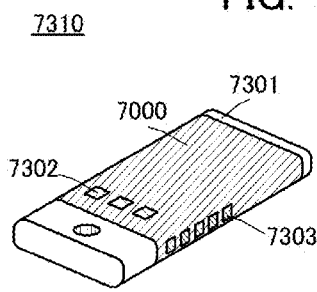
FIG. 14E
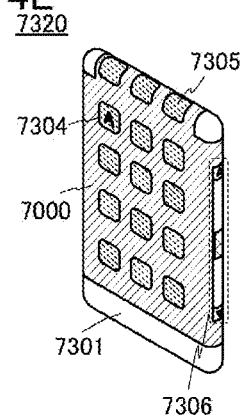
FIG. 14C2
FIG. 14F
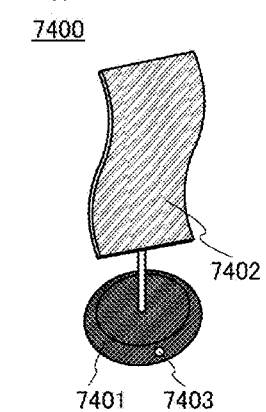
FIG. 14G
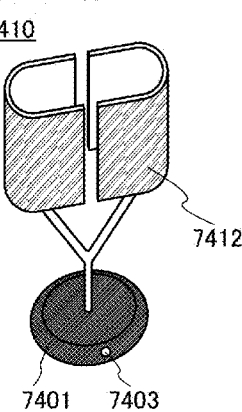
FIG. 14H
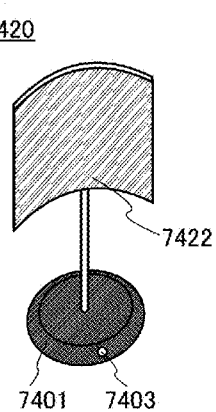

FIG. 15A1
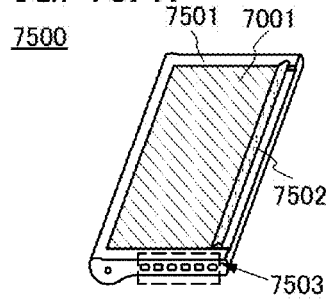
FIG. 15B
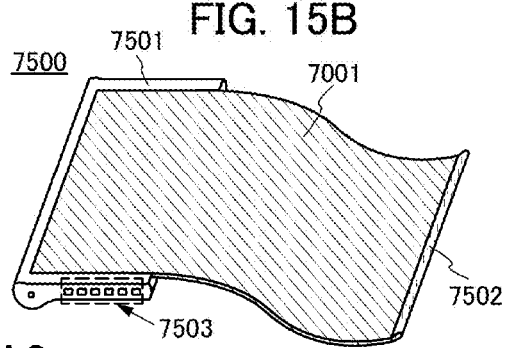
FIG. 15A2
FIG. 15C   FIG. 15D   FIG. 15E
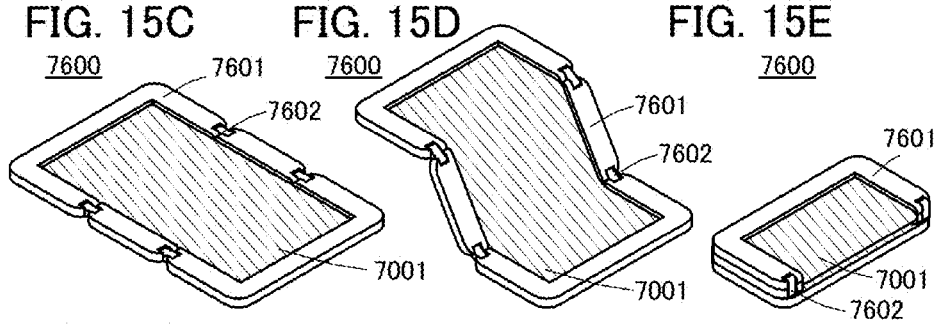
FIG. 15F
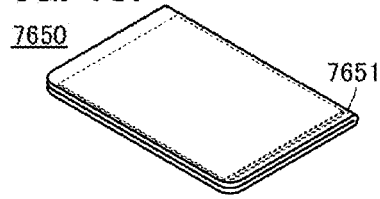
FIG. 15G
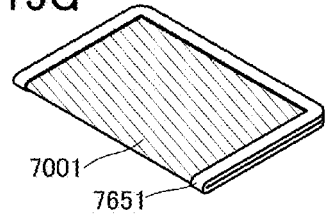
FIG. 15H
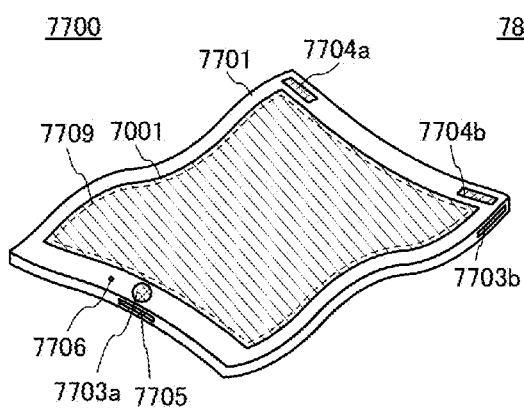
FIG. 15I
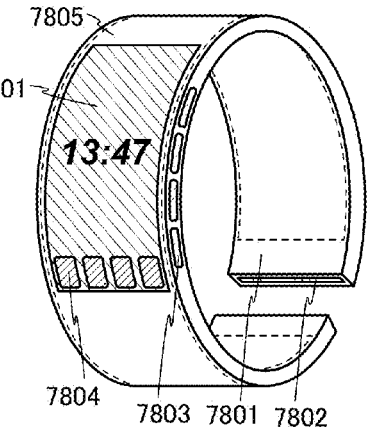

FIG. 17A
FIG. 17B
FIG. 17C
FIG. 17D
FIG. 17E
FIG. 17F
FIG. 17G
FIG. 17H
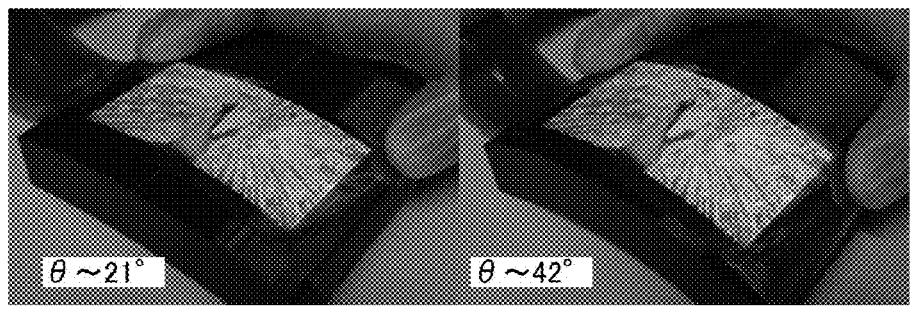
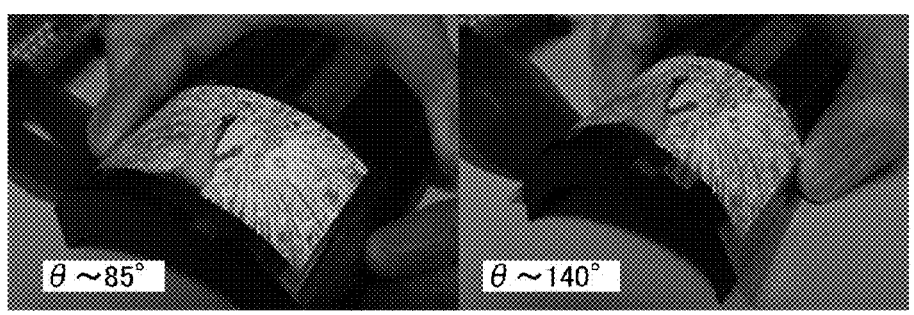
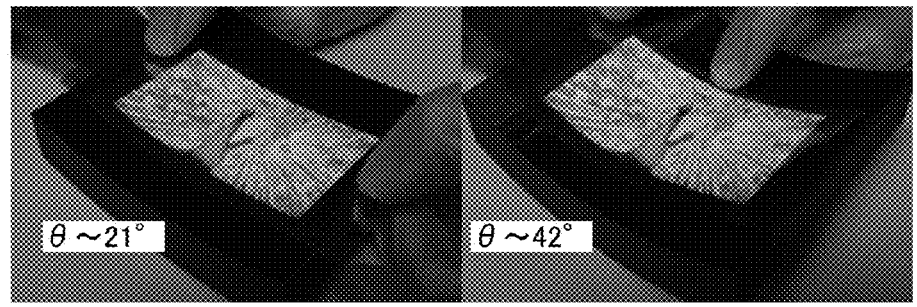
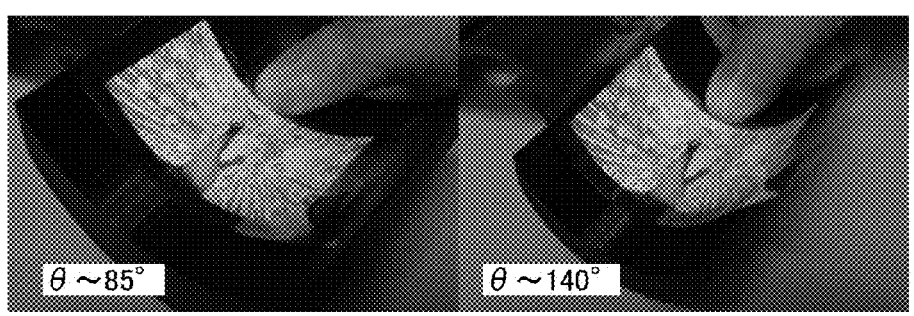

Convex display

Concave display

Convex display

Concave display

DISPLAY DEVICE, MODULE, DISPLAY SYSTEM, AND ELECTRONIC DEVICE

BACKGROUND OF THE INVENTION

1. Field of the Invention

One embodiment of the present invention relates to a display device, a module, a display system, and an electronic device. In particular, one embodiment of the present invention relates to a display device and a display system utilizing organic electroluminescence (hereinafter also referred to as EL).

Note that one embodiment of the present invention is not limited to the above technical field. Examples of the technical field of one embodiment of the present invention include a semiconductor device, a display device, a light-emitting device, a power storage device, a memory device, an electronic device, a lighting device, an input device (e.g., a touch sensor), an input/output device (e.g., a touch panel), a driving method thereof, and a manufacturing method thereof.

2. Description of the Related Art

A variety of display devices have come onto the market, ranging from large-size display devices such as television receivers to small-size display devices such as cellular phones. As higher value added products, display devices capable of displaying three-dimensional images have been actively developed to provide more realistic images.

Physiological factors in human perception of objects in three dimensions include binocular parallax, convergence, focus adjustment, motion parallax, image size, spatial layout, contrast, shading, and the like.

For example, a display device that displays a stereoscopic image using binocular parallax is known. Such a display device is configured to display, on one screen, an image to be seen from the position of the left eye of a viewer (an image for left eye) and an image to be seen from the position of the right eye of the viewer (an image for right eye). The viewer sees the image for left eye with the left eye and the image for right eye with the right eye and is thus allowed to see a stereoscopic image.

As one example of display devices using eyeglasses, there is a display device which displays an image for left eye and an image for right eye alternately on a screen in synchronization with a shutter provided in eyeglasses, whereby the left eye of a viewer is allowed to see only the image for left eye and the right eye of the viewer is allowed to see only the image for right eye. Thus, the viewer can see a stereoscopic image.

Further, in a display device using a parallax barrier which allows a viewer to see a stereoscopic image with naked eyes, a screen is divided into a plurality of regions for left eye and a plurality of regions for right eye (e.g., strip-like regions) arranged side by side. A parallax barrier is provided to overlap with the boundaries of the regions. On the divided screen, an image for left eye and an image for right eye are displayed at the same time. With the parallax barrier, the regions for displaying the image for right eye are hidden from the left eye of a viewer and the regions for displaying the image for left eye are hidden from the right eye of the viewer; consequently, the left eye is allowed to see only the image for left eye and the right eye is allowed to see only the image for right eye. Thus, the viewer can see a stereoscopic image.

Note that a display device including a switchable parallax barrier for achieving switching between a two-dimensional image display mode and a stereoscopic image display mode is known (Patent Document 1).

A light-emitting element utilizing EL is known. This light-emitting element is a self-luminous type; therefore, high contrast and high-speed response to an input signal are achieved. Furthermore, a display device to which this light-emitting element is applied and which consumes less power, is manufactured in a simple process, and is easily adapted to the increase in definition and the size of a substrate is known (Patent Document 2).

REFERENCES

Patent Documents

[Patent Document 1] PCT International Publication No. WO2004/003630
[Patent Document 2] Japanese Published Patent Application No. 2011-238908

SUMMARY OF THE INVENTION

A display device utilizing eyeglasses with shutters displays images for left eye and images for right eye alternately on a screen, which results in an increase in the frequency of image writing to a pixel portion in one frame period as compared with the case of displaying a two-dimensional image. This requires a driver circuit that can be driven at high frequency and also increases the power consumption of the display device.

In a display device with a parallax barrier, the number of pixels that contribute to image display for left eye and the number of pixels that contribute to image display for right eye in the horizontal direction of a pixel portion are reduced to half of the actual number, which prevents high-definition images from being displayed.

Accordingly, it is demanded that a display device can display a two-dimensional image that gives a viewer a strong sense of depth or stereoscopic effect instead of images with binocular parallax such as images for left eye and images for right eye.

Seeing a stereoscopic image displayed on a display device that utilizes binocular parallax sometimes causes a viewer eyestrain, discomfort, headache, visually induced motion sickness, or the like.

It is an object of one embodiment of the present invention to give a viewer a strong stereoscopic effect or sense of depth in a two-dimensional image. It is another object of one embodiment of the present invention to give a viewer a natural stereoscopic effect or sense of depth in a two-dimensional image.

It is another object of one embodiment of the present invention to provide a novel display device or display system. It is another object of one embodiment of the present invention to provide a display device or display system with which a viewer can feel a strong stereoscopic effect or sense of depth in a two-dimensional image. It is another object of one embodiment of the present invention to provide a display device or display system with which a viewer can feel a natural stereoscopic effect or sense of depth in a two-dimensional image. It is another object of one embodiment of the present invention to provide a display device or display system with which a viewer can feel a strong stereoscopic effect or sense of depth in a two-dimensional image and is less likely to be fatigued. It is another object of one embodiment of the present invention to provide a display device or display system with which a viewer can feel a natural stereoscopic effect or sense of depth in a two-dimensional image and is less likely to be fatigued.

Note that the descriptions of these objects do not disturb the existence of other objects. In one embodiment of the present invention, there is no need to achieve all the objects. Other objects can be derived from the description of the specification, the drawings, and the claims.

One embodiment of the present invention is a display device which includes a display portion having a curved surface. The central angle of the curved surface is greater than or equal to 20° and less than 90°.

In the above structure, the definition of the display portion is preferably higher than or equal to 220 ppi and lower than or equal to 2000 ppi.

In the above structure, the contrast ratio of the display portion is preferably 1000:1 or higher.

A device such as a light-emitting device or an input/output device with any of the above structures is also one embodiment of the present invention. These devices include different functional elements in the display portions. For example, the display device of one embodiment of the present invention includes a display element as the functional element. The light-emitting device of one embodiment of the present invention includes a light-emitting element as the functional element. The input/output device of one embodiment of the present invention includes a light-emitting element or a display element, and a touch sensor as the functional elements.

Another embodiment of the present invention is a module which includes the light-emitting device, the display device, or the input/output device with any of the above structures, and a flexible printed circuit (FPC).

Another embodiment of the present invention is a display system which includes a display portion, a detection portion, and a control portion. The display portion is flexible. The detection portion is configured to detect the condition of a viewer's eye to obtain detection information and to supply the detection information to the control portion. The control portion is configured to extract information on the viewer's fatigue from the detection information and to change curvature of the display portion on the basis of the information on the viewer's fatigue.

An electronic device or a lighting device which includes the light-emitting device, the display device, or the input/output device with any of the above structures is also one embodiment of the present invention. For example, one embodiment of the present invention is an electronic device which includes the light-emitting device, the display device, the input/output device, the module, or the display system with any of the above structures, and at least one of an antenna, a battery, a housing, a speaker, a microphone, an operation switch, and an operation button.

According to one embodiment of the present invention, a viewer can feel a strong stereoscopic effect or sense of depth in a two-dimensional image. According to one embodiment of the present invention, a viewer can feel a natural stereoscopic effect or sense of depth in a two-dimensional image.

According to one embodiment of the present invention, a novel display device or display system can be provided. According to one embodiment of the present invention, a display device or display system with which a viewer can feel a strong stereoscopic effect or sense of depth in a two-dimensional image can be provided. According to one embodiment of the present invention, a display device or display system with which a viewer can feel a natural stereoscopic effect or sense of depth in a two-dimensional image can be provided. According to one embodiment of the present invention, a display device or display system with which a viewer can feel a strong stereoscopic effect or sense of depth in a two-dimensional image and is less likely to be fatigued can be provided. According to one embodiment of the present invention, a display device or display system with which a viewer can feel a natural stereoscopic effect or sense of depth in a two-dimensional image and is less likely to be fatigued can be provided.

Note that the description of these effects does not disturb the existence of other effects. One embodiment of the present invention does not necessarily achieve all the effects listed above. Other effects can be derived from the description of the specification, the drawings, and the claims.

BRIEF DESCRIPTION OF THE DRAWINGS

FIGS. 1A1, 1A2, 1B1, 1B2, 1C1, 1C2, 1D1, and 1D2 illustrate examples of a display device.

FIGS. 3A1, 3A2, and 3B illustrate examples of a display device.

FIGS. 7A and 7B illustrate an example of a light-emitting device.

FIGS. 8A to 8D illustrate examples of a light-emitting device.

FIGS. 9A and 9B each illustrate an example of a light-emitting device.

FIGS. 14A, 14B, 14C1, 14C2, 14D, 14E, 14F, 14G, and 14H illustrate examples of an electronic device and a lighting device.

FIGS. 15A1, 15A2, 15B, 15C, 15D, 15E, 15F, 15G, 15H, and 15I illustrate examples of an electronic device.

FIGS. 17A to 17H are photographs of display devices in Example 1.

DETAILED DESCRIPTION OF THE INVENTION

Figure 2A:
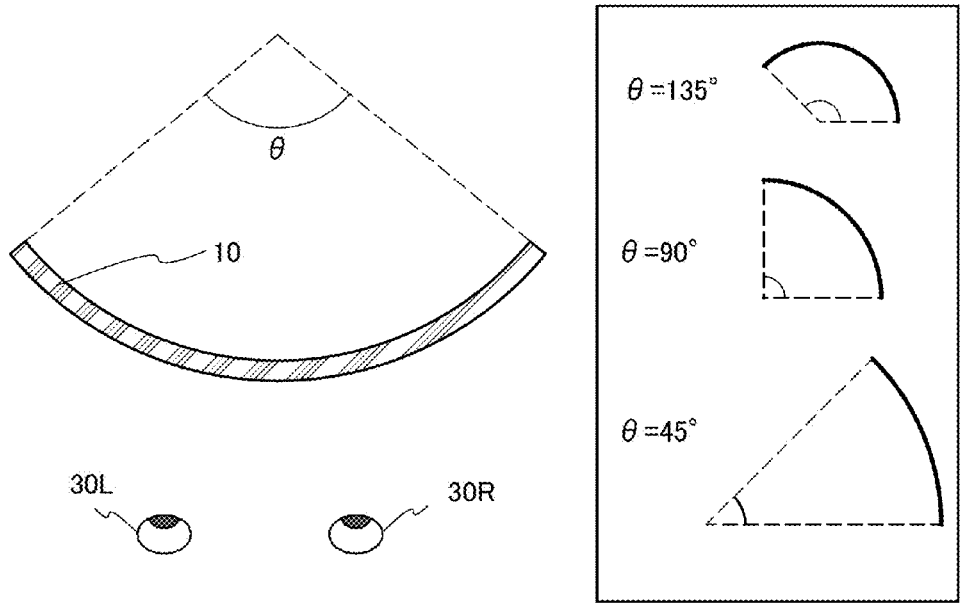
FIGS. 2A and 2B each illustrate a central angle.

Embodiments will be described in detail with reference to the accompanying drawings. Note that the present invention is not limited to the description below, and it is easily understood by those skilled in the art that various changes and modifications can be made without departing from the spirit and scope of the present invention. Therefore, the present invention should not be construed as being limited to the description in the following embodiments.

Note that in the structures of the invention described below, the same portions or portions having similar functions are denoted by the same reference numerals in different drawings, and description of such portions is not repeated. Further, the same hatching pattern is applied to portions having similar functions, and the portions are not especially denoted by reference numerals in some cases.

The position, size, range, or the like of each structure illustrated in drawings is not accurately represented in some cases for easy understanding. Therefore, the disclosed invention is not necessarily limited to the position, size, range, or the like disclosed in the drawings.

Note that the terms "film" and "layer" can be interchanged with each other depending on the case or circumstances. For example, the term "conductive film" can be used instead of the term "conductive layer," and the term "insulating layer" can be used instead of the term "insulating film."

(Embodiment 1)

In this embodiment, a display device and a display system of one embodiment of the present invention will be described with reference to FIGS. 1A1, 1A2, 1B1, 1B2, 1C1, 1C2, 1D1, and 1D2, FIGS. 2A and 2B, FIGS. 3A1, 3A2, and 3B, FIGS. 4A to 4C, and FIGS. 5A and 5B.

Note that a display device will be described as an example in this embodiment; however, one embodiment of the present invention can also be applied to a light-emitting device and an input/output device. In Embodiment 2 and Embodiment 3, a light-emitting device and an input/output device to which one embodiment of the present invention can be applied will be described.

One embodiment of the present invention is a display device which includes a display portion having a curved surface.

In some display devices, a phenomenon called natural3D or n3D (both of them are registered trademarks) occurs in which a viewer can feel a natural stereoscopic effect in a two-dimensional image without utilizing binocular parallax.

A viewer can feel a stronger stereoscopic effect in a two-dimensional image displayed on a bent (curved) display portion than that on a flat display portion.

The display portion may be bent in either the horizontal direction or the vertical direction. Furthermore, the display portion may have either a convex surface (convex curved surface) or a concave surface (concave curved surface) on the display surface side (or viewer side).

The display portion may be flexible; for example, the display portion may be bendable in either the horizontal direction or the vertical direction. Furthermore, the display portion may have either a convex surface or a concave surface on the display surface side. In the case where the display portion is flexible, an image may be displayed in the state where the display portion is not bent (in the state where the display portion is flat). For example, the display device of one embodiment of the present invention can be used in the following manner: the display portion is bent so as to have a curved surface when a stereoscopic image is wanted to be seen, and the display portion is put in a flat state when a stereoscopic image does not need to be seen.

The display portion may be controlled by a viewer himself/herself and/or the display device or the display portion automatically. The display portion may be configured to be curved while reproducing an image. Alternatively, the display portion may be configured to have a constant shape while reproducing an image and to be bendable while not reproducing an image.

FIGS. 1A1, 1A2, 1B1, 1B2, 1C1, 1C2, 1D1, and 1D2 illustrate examples of a display device of one embodiment of the present invention. Note that in each of FIGS. 1A2, 1B2, 1C2, and 1D2, a display surface of the display device is positioned on the viewer (a right eye 30R and a left eye 30L) side.

A display device 110 illustrated in FIGS. 1A1 and 1A2 includes a display portion 101 and a non-display portion 102. The display portion 101 is bent in the horizontal direction (here, in the long-axis direction of the display portion 101) and has a convex surface (convex curved surface) on the display surface side (viewer side).

A display device 111 illustrated in FIGS. 1B1 and 1B2 includes the display portion 101 and the non-display portion 102. The display portion 101 is bent in the horizontal direction and has a concave surface (concave curved surface) on the display surface side (viewer side).

A display device 112 illustrated in FIGS. 1C1 and 1C2 includes the display portion 101 and the non-display portion 102. The display portion 101 is bent in the vertical direction (here, in the short-axis direction of the display portion 101) and has a convex surface on the display surface side (viewer side).

A display device 113 illustrated in FIGS. 1D1 and 1D2 includes the display portion 101 and the non-display portion 102. The display portion 101 is bent in the vertical direction and has a concave surface on the display surface side (viewer side).

In any of the structures in FIGS. 1A1, 1B1, 1C1, and 1D1, a viewer can feel a strong stereoscopic effect or sense of depth in a two-dimensional image. The display portion is preferably bent in the horizontal direction because a strong stereoscopic effect or sense of depth can be obtained as compared with the case where the display portion is bent in the vertical direction. Furthermore, the display portion preferably has a convex surface on the viewer side because a strong stereoscopic effect or sense of depth can be obtained as compared with the case where the display portion has a concave surface on the viewer side.

One embodiment of the present invention is a display device which includes a display portion having a curved surface. The central angle of the curved surface is greater than or equal to 20° and less than or equal to 145°. A viewer can feel a strong stereoscopic effect or sense of depth in a two-dimensional image displayed on such a display device.

Another embodiment of the present invention is a display device which includes a display portion having a curved surface. The central angle of the curved surface is greater than or equal to 20° and less than 90°. The central angle is preferably greater than or equal to 25° and less than or equal to 65°, more preferably greater than or equal to 35° and less than or equal to 55°. A viewer can feel a natural stereoscopic effect or sense of depth in a two-dimensional image displayed on such a display device. Furthermore, a viewer is less likely to be fatigued with a stereoscopic effect or sense of depth in a two-dimensional image displayed on such a display device.

Figure 2B:
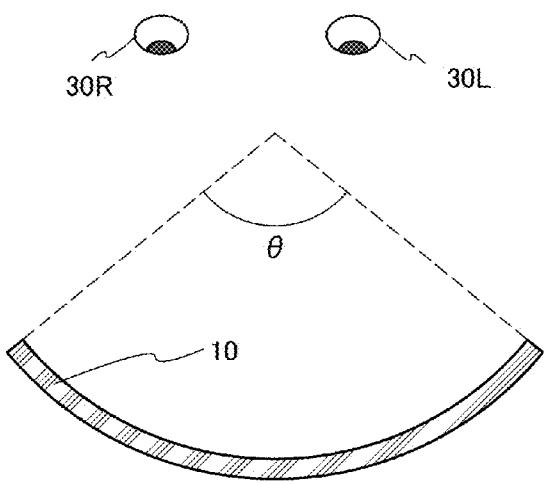

The central angle of a curved surface will be described with reference to FIGS. 2A and 2B. FIG. 2A illustrates an example of a central angle in the case where a convex surface is provided on the display surface side (viewer side), whereas FIG. 2B illustrates an example of a central angle in the case where a concave surface is provided on the display surface side (viewer side). As illustrated in FIGS. 2A and 2B, a display device 10 of one embodiment of the present invention has a curved surface. In this specification and the like, the central angle of a curved surface refers to a central angle θ of an arc of the curved surface. Note that in the case where a display device, a display portion, or a curved surface does not completely agree with part of a circle, the central angle θ of an arc whose shape is the closest to the shape of the display device, the display portion, or the curved surface can be regarded as the central angle of the curved surface.

As shown in the frame on the right side in FIG. 2A, the larger the central angle of a curved surface is, the smaller the radius of curvature is (i.e., the larger the curvature is).

When the central angle of a curved surface is too large, a viewer is likely to be fatigued in some cases. On the other hand, when the central angle of a curved surface is too small, a viewer is less likely to feel a stereoscopic effect in a two-dimensional image in some cases. Therefore, the central angle is preferably as close to 45° as possible.

Like a display device 114 illustrated in FIGS. 3A1 and 3A2, a display device of one embodiment of the present invention may include the display portion 101 having a plurality of curved surfaces. The display portion 101 is bent in the horizontal direction and has a convex surface and a concave surface on the display surface side.

Like a display device 115 illustrated in FIG. 3B, a display device of one embodiment of the present invention does not necessarily have a bend line which is parallel or perpendicular to a side of the display device or a display portion and may be bent in an oblique direction.

Next, results of subjective evaluation experiments for examining stereoscopic effects that viewers feel in two-dimensional images will be described. Note that the number of subjects is 10 or more in each experiment.

For example, with the use of a high-definition display portion, a viewer can feel a stereoscopic effect in a two-dimensional image.

Specifically, the definition of the display portion is preferably 220 ppi or higher because a strong stereoscopic effect can be obtained in a two-dimensional image.

In the experiment for examining the relationship between a definition and a stereoscopic effect that viewers feel, a 3.93-inch organic EL display having a definition of 458 ppi was used as a display device. The visual distance was 30 cm, and the experiment was carried out in a dark place. The experimental results revealed that a stereoscopic effect that the viewers felt in a moving image having a definition of 229 ppi was stronger than that the viewers felt in a moving image having a definition of 114.5 ppi; furthermore, a stereoscopic effect that the viewers felt in a moving image having a definition of 458 ppi was equivalent to that the viewers felt in the moving image having a definition of 229 ppi. Accordingly, the viewers can easily feel a stereoscopic effect in a two-dimensional image when the definition of the image is sufficiently high.

As described above, a stereoscopic effect obtained from an image does not necessarily become stronger by increasing the definition of an image as much as possible. For example, the definition of the display portion can be higher than or equal to 220 ppi and lower than or equal to 2000 ppi. The definition is preferably higher than 2000 ppi depending on the intended use of a display, like in the case of a head-mounted display.

For example, in order for a viewer having 20/20 vision to feel a strong stereoscopic effect in a two-dimensional image, the angular resolution is preferably 20 cpd or higher, more preferably 30 cpd or higher, still more preferably 60 cpd or higher.

When a display portion with high contrast is used, a viewer can feel a stereoscopic effect in a two-dimensional image.

Specifically, the contrast ratio of the display portion is preferably 1000:1 or higher.

A stereoscopic effect that the viewers felt in an image became weaker when the luminance of black displayed in the viewed display device was gradually changed from a minimum value to a higher value. For this reason, the higher the contrast ratio of a two-dimensional image is, the more likely the viewers are to feel stereoscopic effects in the image.

When the degree of curvature of a display portion in a display device is constant, malfunction sometimes occurs. For example, in some cases, a stereoscopic effect or sense of depth differs among viewers, and an appropriate range of curvature of the display portion varies between individuals. In the case where the degree of curvature of the display portion is not suitable for a viewer, the viewer is sometimes less likely to feel a stereoscopic effect or sense of depth in a two-dimensional image when viewing the display portion. When the stereoscopic effect or sense of depth is too strong, the brain and eyes might be severely strained so that the viewer feels fatigued a lot. Furthermore, depending on an image displayed on the display portion, a stereoscopic effect or sense of depth that the viewer feels might be stronger or weaker without the intention or might be constant despite the intention.

In view of the above, in the display device of one embodiment of the present invention, the degree of curvature of the display portion is made variable. Accordingly, the degree of curvature of the display portion can be adjusted such that a viewer can feel a natural stereoscopic effect and can be less likely to be fatigued. For example, the degree of curvature of the display portion can be adjusted according to how much a viewer is fatigued. Furthermore, by adjusting the degree of curvature of the display portion according to an image displayed on the display portion, a stereoscopic effect or sense of depth can be prevented from being stronger or weaker without the intention or can be stronger or weaker by the intention. Consequently, a viewer can feel a strong stereoscopic effect or sense of depth in a two-dimensional image displayed on the display device of one embodiment of the present invention, and can be less likely to be fatigued therewith.

Figure 4A:
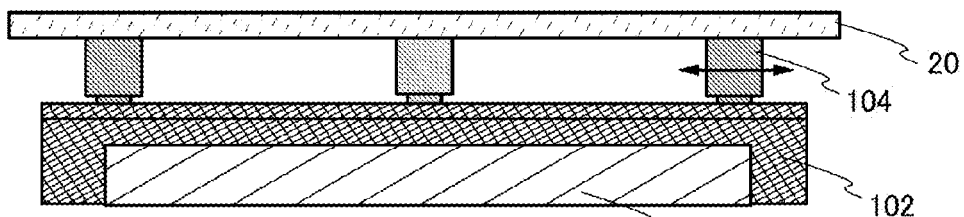
FIGS. 4A to 4C illustrate an example of a display device.
Figure 4B:
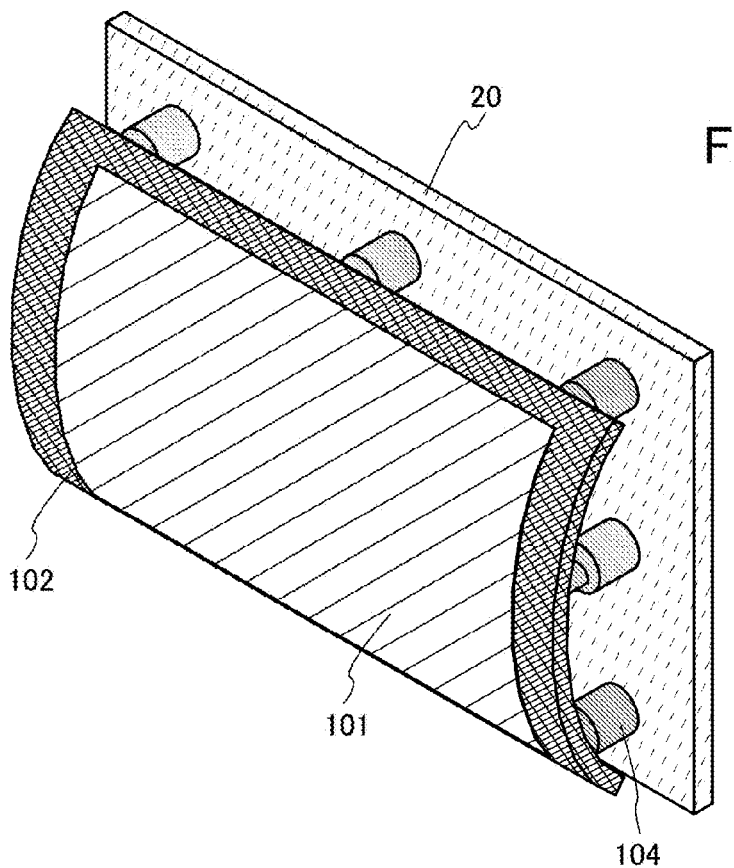
Figure 4C:
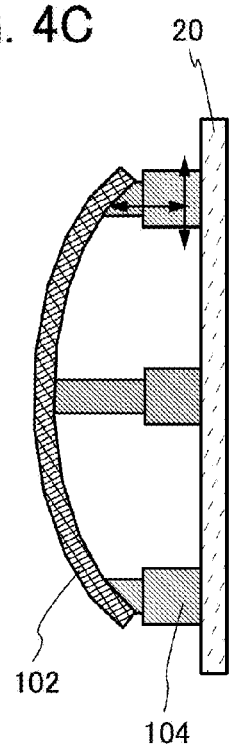

FIGS. 4A to 4C illustrate a display device of another embodiment of the present invention. FIG. 4A is a top view of the display device, FIG. 4B is a perspective view thereof, and FIG. 4C is a side view thereof.

The display device in FIGS. 4A to 4C includes the display portion 101 and the non-display portion 102 each having flexibility, and a plurality of driver portions 104. The driver portions 104 can be driven independently of each other. The degree, the direction, or the like of curvature of the display portion 101 can be adjusted by changing the lengths or the positions of the driver portions 104 attached to a structure body 20. The driver portions 104 may be movable on the surface of the structure body 20 in the vertical direction and the horizontal direction as indicated by arrows. The lengths of the driver portions 104 in the direction perpendicular to the surface of the structure body 20 may be variable. A contact point between the driver portion 104 and the display portion 101 or the non-display portion 102 may be moved.

There is no particular limitation on the number of driver portions. In the case where the number of driver portions is two or more, the driver portions are driven independently of each other, or part or all of them are driven in synchronization with each other.

Note that the driver portions 104 may be attached to a member of the display device, or may be attached to a wall surface or a floor on which the display device is disposed. That is, the structure body 20 may or may not be included in the display device.

Next, a structure example of a display system of one embodiment of the present invention will be described with reference to FIG. 5A.

Figure 5A:
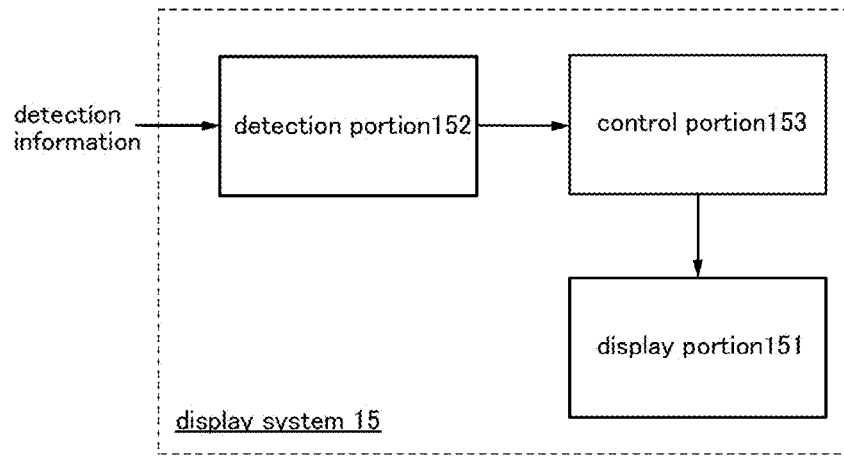
FIGS. 5A and 5B show an example of a display system.

A display system 15 shown in FIG. 5A includes a display portion 151, a detection portion 152, and a control portion 153.

The display portion 151 is flexible. The display portion 151 can display an image in a bent state. For example, the display portion 151 can have a curved surface whose central angle is greater than or equal to 20° and less than or equal to 145°. The display system 15 can be used also in the state where the display portion 151 is flat.

The detection portion 152 has a function of detecting the conditions of a viewer's eye to obtain detection information and a function of supplying the detection information to the control portion 153.

The detection portion 152 includes a detector and a controller.

The driving of the detector is controlled by the controller. The detector can detect the conditions of a viewer's eye and output information on the conditions of the eye (detection information) to the controller.

The conditions of the viewer's eye include the movement of an eyeball, the color or shape of a component (e.g., white of the eye, iris, or pupil) of the eyeball, the movement of an eyelid, or the like of the viewer.

As the detector, a still camera or video camera can be used, for example. In this case, an image of a viewer's eyeball is taken by the still camera or video camera to be output as detection information to the controller.

The detector can have a structure including a light source for emitting infrared light and a light-receiving portion for detecting the infrared light reflected from a viewer's eyeball, for example. The use of infrared light makes it possible to precisely detect the conditions of a viewer's eye without causing strain on the viewer.

The detection portion 152 may detect the focal length or the direction or the like of line of sight of a viewer viewing the display portion.

The controller outputs to the control portion 153 the detection information supplied from the detector.

The control portion 153 has a function of extracting information on the viewer's fatigue from the detection information and a function of changing the degree of curvature of the display portion 151 according to the fatigue information. The degree of curvature of the display portion 151 can be determined on the basis of the size of the display portion 151 and the curvature, the radius of curvature, or the central angle of a curved surface.

Figure 5B:
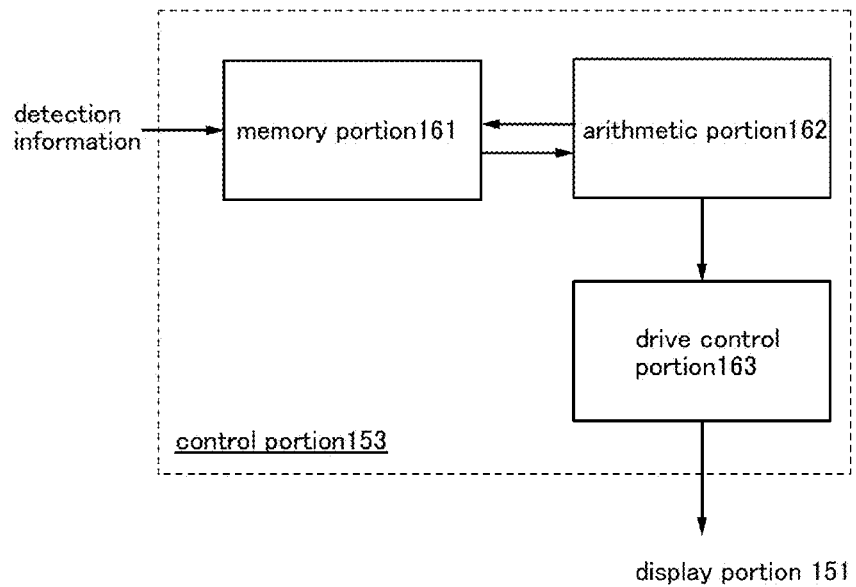

As shown in FIG. 5B, the control portion 153 includes a memory portion 161, an arithmetic portion 162, and a drive control portion 163.

To the memory portion 161, the detection information is supplied from the detection portion 152. The memory portion 161 includes a variety of kinds of memory circuits for storing the detection information, a computer program for making the arithmetic portion 162 execute arithmetic processing, a look-up table, arithmetic results, or the like.

The memory portion 161 can store, for example, information for determining the processing that the arithmetic portion 162 executes. For example, the memory portion 161 can store information for determining, on the basis of the viewer's fatigue conditions, whether or not the curvature of the display portion 151 is changed. Furthermore, the memory portion 161 may store a parameter for setting the degree of changing the curvature of the display portion 151, the frequency of detecting fatigue conditions, the threshold value for determining fatigue conditions, or the like. It is preferred that the above information can be changed as appropriate by a user of the display system.

To the arithmetic portion 162, the detection information is supplied from the memory portion 161. The arithmetic portion 162 generates a control signal by analyzing the supplied detection information.

The arithmetic portion 162 extracts information on the viewer's fatigue from the detection information, and controls the operation of the drive control portion 163 on the basis of the information on the viewer's fatigue such that the degree of curvature of the display portion 151 is changed.

Examples of the information on the viewer's fatigue include the length of screen gazing time and the number of times of blinking per unit time of the viewer. In addition, the amplitude or frequency of nystagmus, the degree of inflammation of an eyeball, the area of a pupil, and the frequency of convulsions of an eyelid or the like can be used as the information on the viewer's fatigue. Other examples of the information on the viewer's fatigue are gestures which are physiologically likely to be made owing to fatigue, for example, a gesture of closing one's eyelids for a long time (e.g., one second or longer) or a gesture of pressing one's eye area with a finger or the like, and the frequency of such gestures. The arithmetic portion 162 extracts, as data, such information on the viewer's fatigue included in the detection information.

The arithmetic portion 162 may read out information for determining the processing that the arithmetic portion 162 executes and is stored in the memory portion 161. In this case, the arithmetic portion 162 executes an arithmetic operation on the basis of both such information and information on the viewer's fatigue extracted from the detection information.

Here, the information on the viewer's fatigue extracted by the arithmetic portion 162 is preferably divided into levels (fatigue levels) according to the viewer's fatigue conditions. In this case, the degree of curvature of the display portion 151 is changed according to the corresponding fatigue level. For example, when the fatigue level of the viewer is higher, the central angle is made smaller (i.e., the radius of curvature is made larger or the curvature is made smaller).

The fatigue level may be updated stepwise when the viewer's fatigue conditions are maintained for a certain period. For example, the central angle is made smaller when the viewer is kept fatigued for a certain period.

In this manner, the degree of correction is increased stepwise according to the fatigue level or the length of the period during which the fatigue continues; such operation makes it possible to relieve accumulation of the viewer's fatigue and further reduce the fatigue even in long-term use of the display device.

In the case where the viewer's fatigue is detected, the degree of curvature of the display portion is changed, and in addition, the viewer may be noticed that he/she is fatigued. The viewer can be noticed that he/she is fatigued when the display portion 151 displays it or a speaker outputs sound, for example. Such notice can encourage the viewer to stop using the display device, whereby accumulation of eyestrain can be prevented.

A control signal generated in the arithmetic portion 162 is supplied to the drive control portion 163, and the degree of curvature of the display portion 151 can be controlled on the basis of the control signal. The display portion 151 may be moved directly. Alternatively, the display portion 151 may be moved indirectly in such a manner that the driver portions illustrated in FIGS. 4A to 4C are moved.

An example of a procedure of the operation of the display system 15 will be described.

First, the display portion 151 performs display.

Next, the detection portion 152 detects the conditions of a viewer's eye to obtain detection information. It is preferred that the detection portion 152 perform detection continuously in a period during which the display portion 151 performs display or perform detection at intervals of a certain period.

The detection portion 152 supplies the control portion 153 with the detection information.

The control portion 153 extracts fatigue information as data from the detection information. The control portion 153 determines whether the curvature of the display portion 151 needs to be changed on the basis of the fatigue information. In the case where it is determined that the curvature of the display portion 151 needs to be changed, the control portion 153 makes the curvature of the display portion 151 changed.

The control portion 153 may make the degree, direction, or the like of the curvature of the display portion 151 changed with the use of information other than the information detected by the detection portion 152. For example, the degree, direction, or the like of the curvature of the display portion 151 can be changed according to the content of a moving image, which is preferable because a viewer can feel a stronger stereoscopic effect or sense of depth in a two-dimensional image.

Specifically, when a moving image in which a moving object seems to approach a viewer is displayed, the display portion 151 is preferably transformed so as to have a convex surface on the viewer side.

For example, image data to be displayed on the display portion 151 may be supplied to the control portion 153. It is preferred that the arithmetic portion 162 can generate a control signal by analyzing the supplied image data.

As the analysis of image data, specifically, spectrum analysis (such as content analysis), and detection of expansion or movement (zoom in/zoom out, pan/tilt (panning), detection of movement speed, or detection of movement direction) can be given.

In the case where audio data is supplied to the arithmetic portion 162, the arithmetic portion 162 is preferably configured to generate a control signal by analyzing the supplied audio data. Note that a control signal is preferably generated on the basis of analysis results of both image data and audio data.

As the analysis of audio data, specifically, spectrum analysis (such as content analysis), sound source analysis, and separate extraction of music, human voice, or the like can be given.

In the case where data on results of sensitivity evaluation of a stereoscopic effect, a feeling of fatigue, or the like is supplied to the arithmetic portion 162, the arithmetic portion 162 is preferably configured to analyze the data to generate a control signal.

For example, a plurality of users of a display system are subjected to sensitivity evaluation in advance so that what curved surface of a display portion can easily provide a strong stereoscopic effect is examined When using the display system, each user selects own data obtained in the sensitivity evaluation. Then, a control signal generated by analysis of the data in the arithmetic portion 162 is supplied from the arithmetic portion 162 to the control portion. On the basis of the control signal, the driver control portion transforms the display portion so that the display portion can have a curved surface suitable for the user.

It is preferred that a viewer can select the intensity or existence of a stereoscopic effect, the degree of curvature of the display portion, or the like and a signal based on the selection can be supplied to the control portion 153. A control signal based on such a signal may be generated in the arithmetic portion 162.

<DISPLAY PORTION>

A display device of one embodiment of the present invention includes a display portion capable of displaying an image in a plane. Note that an image in this specification may be either a still image or a moving image (video).

There is no particular limitation on the display portion as long as it has a curved surface. The display portion is preferably flexible, in which case the shape, curvature, or the like of the curved surface can be made variable.

The display portion may include a display element. Examples of the display portion or the display element in the display portion include an EL element (e.g., an EL element including organic and inorganic materials, an organic EL element, or an inorganic EL element), an LED (e.g., a white LED, a red LED, a green LED, or a blue LED), a transistor (a transistor which emits light depending on current), an electron emitter, a liquid crystal element, electronic ink, an electrophoretic element, and a display element using micro electro mechanical systems (MEMS). Examples of a display portion having an EL element include an EL display. Examples of display portions including liquid crystal elements include a liquid crystal display (e.g., a transmissive liquid crystal display, a transflective liquid crystal display, a reflective liquid crystal display, a direct-view liquid crystal display, or a projection liquid crystal display). Examples further include a display portion including electronic ink or an electrophoretic element, such as electronic paper.

An organic EL display as a display portion is likely to offer a viewer a stronger stereoscopic effect or sense of depth in a two-dimensional image than a liquid crystal display. Therefore, one embodiment of the present invention is preferably applied to an organic EL display, particularly a flexible organic EL display.

The resolution of the display portion is preferably as high as FHD (1920×1080), 4K2K (e.g., 3840×2048 or 4096×2180), or 8K4K (e.g., 7680×4320 or 8192×4320), for example.

A non-display portion of a display device of one embodiment of the present invention may include, for example, a sealing region or a driver circuit of a display element or a light-emitting element.

A display device of one embodiment of the present invention can be used in amusement facilities (e.g., an amusement park, an amusement arcade, or a theme park), theaters, movie theaters, and the like. For example, the degree of curvature of a display portion is changed according to the content of attraction, whereby a viewer can feel a strong stereoscopic effect or sense of depth in a two-dimensional image.

As described above, a viewer can feel a strong stereoscopic effect or sense of depth in a two-dimensional image displayed on a display portion with a curved surface in a display device of one embodiment of the present invention. Furthermore, since the degree of curvature of a display portion can be changed in a display device of one embodiment of the present invention, a viewer can feel a strong stereoscopic effect or sense of depth in a two-dimensional image, which does not vary between individuals or according to display content. In addition, the degree of curvature of a display portion can be adjusted by a viewer or a display system so that the curvature of the display portion can be suitable for the viewer; thus, the viewer is less likely to be fatigued therewith than in the case where a display portion the degree of curvature of which is not suitable for the viewer is used.

This embodiment can be combined with any of the other embodiments as appropriate.

(Embodiment 2)

In this embodiment, a light-emitting device of one embodiment of the present invention will be described with reference to drawings.

Although a light-emitting device mainly including an organic EL element is described in this embodiment as an example, one embodiment of the present invention is not limited to this example.

When the light-emitting device described in this embodiment is bent, the minimum radius of curvature of a bent portion of the light-emitting device can be greater than or equal to 1 mm and less than or equal to 150 mm, greater than or equal to 1 mm and less than or equal to 100 mm, greater than or equal to 1 mm and less than or equal to 50 mm, greater than or equal to 1 mm and less than or equal to 10 mm, or greater than or equal to 2 mm and less than or equal to 5 mm. The light-emitting device in this embodiment is free from breakage of an element even when bent with a small radius of curvature (e.g., greater than or equal to 2 mm and less than or equal to 5 mm) and has high reliability. There is no limitation on the direction in which the light-emitting device in this embodiment is bent. Further, the number of bent portions may be one or more than one.

The light-emitting device of one embodiment of the present invention can provide a strong or natural stereoscopic effect in a two-dimensional image. Furthermore, the light-emitting device of one embodiment of the present invention can provide a strong or natural stereoscopic effect in a two-dimensional image and is less likely to make a viewer fatigued.

SPECIFIC EXAMPLE 1

Figure 6A:
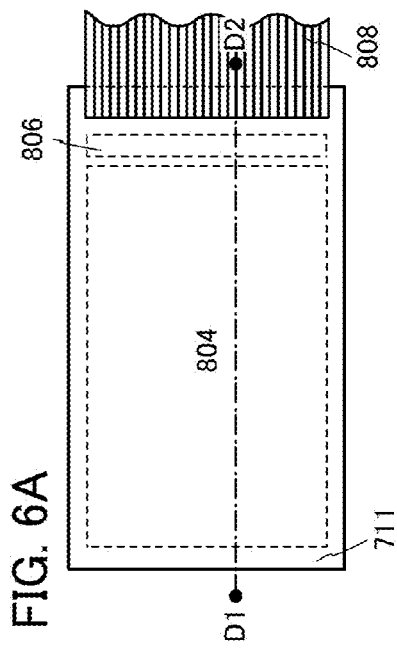
FIGS. 6A and 6B illustrate an example of a light-emitting device.
Figure 6B:
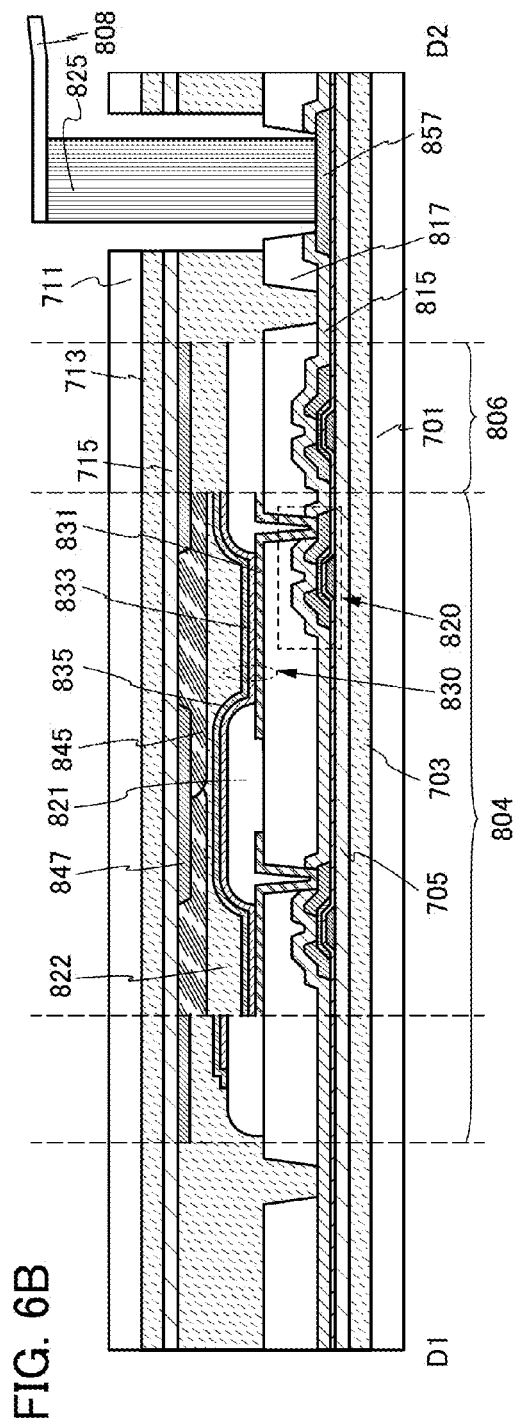

FIG. 6A is a plan view of a light-emitting device, and FIG. 6B is an example of a cross-sectional view taken along dashed-dotted line D1-D2 in FIG. 6A. The light-emitting device in Specific Example 1 is a top-emission light-emitting device using a color filter method. In this embodiment, the light-emitting device can have a structure in which subpixels of three colors of red (R), green (G), and blue (B), for example, express one color; a structure in which subpixels of four colors of R, G, B, and white (W) express one color; a structure in which subpixels of four colors of R, G, B, and yellow (Y) express one color; or the like. There is no particular limitation on color elements, and colors other than R, G, B, W, and Y may be used. For example, cyan or magenta may be used.

The light-emitting device illustrated in FIG. 6A includes a light-emitting portion 804, a driver circuit portion 806, and an FPC 808.

The light-emitting device illustrated in FIG. 6B includes a first flexible substrate 701, a first bonding layer 703, a first insulating layer 705, a first functional layer (a plurality of transistors, a conductive layer 857, an insulating layer 815, an insulating layer 817, a plurality of light-emitting elements, and an insulating layer 821), a third bonding layer 822, a second functional layer (a coloring layer 845 and a light-blocking layer 847), a second insulating layer 715, a second bonding layer 713, and a second flexible substrate 711. The third bonding layer 822, the second insulating layer 715, the second bonding layer 713, and the second flexible substrate 711 transmit visible light. Light-emitting elements and transistors in the light-emitting portion 804 and the driver circuit portion 806 are sealed with the first flexible substrate 701, the second flexible substrate 711, and the third bonding layer 822.

In the light-emitting portion 804, a transistor 820 and a light-emitting element 830 are provided over the first flexible substrate 701 with the first bonding layer 703 and the first insulating layer 705 placed therebetween. The light-emitting element 830 includes a lower electrode 831 over the insulating layer 817, an EL layer 833 over the lower electrode 831, and an upper electrode 835 over the EL layer 833. The lower electrode 831 is electrically connected to a source electrode or a drain electrode of the transistor 820. An end portion of the lower electrode 831 is covered with the insulating layer 821. The lower electrode 831 preferably reflects visible light. The upper electrode 835 transmits visible light.

In the light-emitting portion 804, the coloring layer 845 overlapping with the light-emitting element 830 and the light-blocking layer 847 overlapping with the insulating layer 821 are provided. The space between the light-emitting element 830 and the coloring layer 845 is filled with the third bonding layer 822.

The insulating layer 815 has an effect of preventing diffusion of impurities into a semiconductor included in the transistor. As the insulating layer 817, an insulating layer having a planarization function is preferably used in order to reduce surface unevenness due to the transistor.

In the driver circuit portion 806, a plurality of transistors are provided over the first flexible substrate 701 with the first bonding layer 703 and the first insulating layer 705 positioned therebetween. FIG. 6B illustrates one of the transistors included in the driver circuit portion 806.

The first insulating layer 705 and the first flexible substrate 701 are attached to each other with the first bonding layer 703. The second insulating layer 715 and the second flexible substrate 711 are attached to each other with the second bonding layer 713. At least one of the first insulating layer 705 and the second insulating layer 715 is preferably highly resistant to moisture, in which case impurities such as water can be prevented from entering the light-emitting element 830 or the transistor 820, leading to higher reliability of the light-emitting device.

The conductive layer 857 is electrically connected to an external input terminal through which a signal or a potential from the outside is transmitted to the driver circuit portion 806. Here, an example in which the FPC 808 is provided as the external input terminal is described. To prevent an increase in the number of fabrication steps, the conductive layer 857 is preferably formed using the same material and the same step as the electrode or the wiring in the light-emitting portion and the driver circuit portion. Here, an example is described in which the conductive layer 857 is formed using the same material and the same step as the electrodes of the transistor 820.

In the light-emitting device in FIG. 6B, the FPC 808 is positioned over the second flexible substrate 711. A connector 825 is connected to the conductive layer 857 through an opening provided in the second flexible substrate 711, the second bonding layer 713, the second insulating layer 715, the third bonding layer 822, the insulating layer 817, and the insulating layer 815. Furthermore, the connector 825 is connected to the FPC 808. That is, the FPC 808 and the conductive layer 857 are electrically connected to each other through the connector 825. When the conductive layer 857 and the second flexible substrate 711 overlap with each other, an opening formed in the second flexible substrate 711 (or the use of a substrate with an opening) allows the conductive layer 857, the connector 825, and the FPC 808 to be electrically connected to each other.

A modification example of the light-emitting device illustrated in FIGS. 6A and 6B will be described. FIG. 7A is a plan view of a light-emitting device, and FIG. 7B is an example of a cross-sectional view taken along dashed-dotted line D3-D4 in FIG. 7A. FIG. 8A is an example of a cross-sectional view taken along dashed-dotted line D5-D6 in FIG. 7A.

The light-emitting device illustrated in FIGS. 7A and 7B shows an example in which the first flexible substrate 701 and the second flexible substrate 711 have different sizes. The FPC 808 is positioned over the second insulating layer 715 and does not overlap with the second flexible substrate 711. The connector 825 is connected to the conductive layer 857 through an opening provided in the second insulating layer 715, the third bonding layer 822, the insulating layer 817, and the insulating layer 815. There is no limitation on the material for the second flexible substrate 711 because an opening does not need to be provided in the second flexible substrate 711.

It is preferred that the insulating layer formed using an organic resin having a poor gas barrier property or a poor moisture-resistant property not be exposed in an end portion of the light-emitting device. With such a structure, entry of impurities from the side surface of the light-emitting device can be prevented. For example, as illustrated in FIG. 7B and FIG. 8A, the structure in which the insulating layer 817 is not provided in the end portion of the light-emitting device may be employed.

FIG. 8B shows a modification example of the light-emitting portion 804.

The light-emitting device illustrated in FIG. 8B includes insulating layers 817a and 817b and a conductive layer 856 over the insulating layer 817a. The source electrode or the drain electrode of the transistor 820 and the lower electrode of the light-emitting element 830 are electrically connected to each other through the conductive layer 856.

The light-emitting device illustrated in FIG. 8B includes a spacer 823 over the insulating layer 821. The spacer 823 can adjust the distance between the first flexible substrate 701 and the second flexible substrate 711.

The light-emitting device in FIG. 8B includes an overcoat 849 covering the coloring layer 845 and the light-blocking layer 847. The space between the light-emitting element 830 and the overcoat 849 is filled with the bonding layer 822.

FIG. 8C shows a modification example of the light-emitting element 830.

Note that as illustrated in FIG. 8C, the light-emitting element 830 may include an optical adjustment layer 832 between the lower electrode 831 and the EL layer 833. A light-transmitting conductive material is preferably used for the optical adjustment layer 832. Owing to the combination of a color filter (the coloring layer) and a microcavity structure (the optical adjustment layer), light with high color purity can be extracted from the light-emitting device of one embodiment of the present invention. The thickness of the optical adjustment layer is varied depending on the emission color of the subpixel.

SPECIFIC EXAMPLE 2

A light-emitting device illustrated in FIG. 8D includes the first flexible substrate 701, the first bonding layer 703, the first insulating layer 705, a first functional layer (a conductive layer 814, a conductive layer 857a, a conductive layer 857b, the light-emitting element 830, and the insulating layer 821), the second bonding layer 713, and the second flexible substrate 711.

The conductive layer 857a and the conductive layer 857b serve as external connection electrodes of the light-emitting device and can each be electrically connected to an FPC or the like.

The light-emitting element 830 includes the lower electrode 831, the EL layer 833, and the upper electrode 835. An end portion of the lower electrode 831 is covered with the insulating layer 821. The light-emitting element 830 has a bottom-emission structure, a top-emission structure, or a dual-emission structure. The electrode, substrate, insulating layer, and the like through which light is extracted transmit visible light. The conductive layer 814 is electrically connected to the lower electrode 831.

The substrate through which light is extracted may have, as a light extraction structure, a hemispherical lens, a micro lens array, a film provided with an uneven surface structure, a light diffusing film, or the like. For example, the substrate with the light extraction structure can be formed by bonding the above lens or film to a resin substrate with an adhesive or the like having substantially the same refractive index as the substrate, the lens, or the film.

The conductive layer 814 is preferably, though not necessarily, provided because voltage drop due to the resistance of the lower electrode 831 can be inhibited. In addition, for a similar purpose, a conductive layer electrically connected to the upper electrode 835 may be provided over the insulating layer 821, the EL layer 833, the upper electrode 835, or the like.

The conductive layer 814 can be a single layer or a stacked layer formed using a material selected from copper, titanium, tantalum, tungsten, molybdenum, chromium, neodymium, scandium, nickel, and aluminum, an alloy material containing any of these materials as its main component, and the like. The thickness of the conductive layer 814 can be, for example, greater than or equal to 0.1 μm and less than or equal to 3 μm, preferably greater than or equal to 0.1 μm and less than or equal to 0.5 μm.

SPECIFIC EXAMPLE 3

FIG. 7A is a plan view of a light-emitting device. FIG. 9A is an example of a cross-sectional view taken along dashed-dotted line D3-D4 in FIG. 7A. The light-emitting device in Specific Example 3 is a bottom-emission light-emitting device using a color filter method.

The light-emitting device illustrated in FIG. 9A includes the first flexible substrate 701, the first bonding layer 703, the first insulating layer 705, a first functional layer (a plurality of transistors, the conductive layer 857, the insulating layer 815, the coloring layer 845, the insulating layer 817a, the insulating layer 817b, the conductive layer 856, a plurality of light-emitting elements, and the insulating layer 821), the second bonding layer 713, and the second flexible substrate 711. The first flexible substrate 701, the first bonding layer 703, the first insulating layer 705, the insulating layer 815, the insulating layer 817a, and the insulating layer 817b transmit visible light.

In the light-emitting portion 804, the transistor 820, a transistor 824, and the light-emitting element 830 are provided over the first flexible substrate 701 with the first bonding layer 703 and the first insulating layer 705 positioned therebetween. The light-emitting element 830 includes the lower electrode 831 over the insulating layer 817b, the EL layer 833 over the lower electrode 831, and the upper electrode 835 over the EL layer 833. The lower electrode 831 is electrically connected to the source electrode or the drain electrode of the transistor 820. An end portion of the lower electrode 831 is covered with the insulating layer 821. The upper electrode 835 preferably reflects visible light. The lower electrode 831 transmits visible light. There is no particular limitation on the position of the coloring layer 845 overlapping with the light-emitting element 830; for example, the coloring layer 845 can be provided between the insulating layer 817a and the insulating layer 817b or between the insulating layer 815 and the insulating layer 817a.

In the driver circuit portion 806, a plurality of transistors are provided over the first flexible substrate 701 with the first bonding layer 703 and the first insulating layer 705 positioned therebetween. FIG. 9A illustrates two of the transistors in the driver circuit portion 806.

The first insulating layer 705 and the first flexible substrate 701 are attached to each other with the first bonding layer 703. The first insulating layer 705 is preferably highly resistant to moisture, in which case impurities such as water can be prevented from entering the light-emitting element 830, the transistor 820, or the transistor 824, leading to higher reliability of the light-emitting device.

The conductive layer 857 is electrically connected to an external input terminal through which a signal or a potential from the outside is transmitted to the driver circuit portion 806. In this example, the FPC 808 is provided as the external input terminal, and the conductive layer 857 is formed using the same material and the same step as the conductive layer 856.

SPECIFIC EXAMPLE 4

FIG. 7A is a plan view of a light-emitting device. FIG. 9B is an example of a cross-sectional view taken along dashed-dotted line D3-D4 in FIG. 7A. The light-emitting device in Specific Example 4 is a top-emission light-emitting device using a separate coloring method.

The light-emitting device in FIG. 9B includes the first flexible substrate 701, the first bonding layer 703, the first insulating layer 705, a first functional layer (a plurality of transistors, the conductive layer 857, the insulating layer 815, the insulating layer 817, a plurality of light-emitting elements, the insulating layer 821, and the spacer 823), the second bonding layer 713, and the second flexible substrate 711. The second bonding layer 713 and the second flexible substrate 711 transmit visible light.

In the light-emitting device illustrated in FIG. 9B, the connector 825 is positioned over the insulating layer 815. The connector 825 is connected to the conductive layer 857 through an opening provided in the insulating layer 815. The connector 825 is also connected to the FPC 808. That is, the FPC 808 and the conductive layer 857 are electrically connected to each other through the connector 825.

EXAMPLES of MATERIALS

Next, materials that can be used for the light-emitting device will be described. Note that description of the components already described in this specification is omitted in some cases.

For the substrates, glass, quartz, an organic resin, a metal, an alloy, or the like can be used. The substrate through which light from the light-emitting element is extracted is formed using a material that transmits the light.

It is particularly preferable to use a flexible substrate. For example, it is possible to use glass, a metal, or an alloy that is thin enough to have flexibility, or an organic resin. For example, the thickness of the flexible substrate is preferably greater than or equal to 1 µm and less than or equal to 200 µm, further preferably greater than or equal to 1 µm and less than or equal to 100 µm, still further preferably greater than or equal to 10 µm and less than or equal to 50 µm, and particularly preferably greater than or equal to 10 µm and less than or equal to 25 µm.

An organic resin, which has a smaller specific gravity than glass, is preferably used for the flexible substrate, in which case the light-emitting device can be lighter in weight than that using glass.

A material with high toughness is preferably used for the substrates. In that case, a light-emitting device with high impact resistance that is less likely to be broken can be provided. For example, when an organic resin substrate or a metal or alloy substrate with a small thickness is used, the light-emitting device can be lightweight and less likely to be broken as compared with the case where a glass substrate is used.

A metal material and an alloy material, which have high thermal conductivity, are preferred because they can easily conduct heat to the whole substrate and accordingly can prevent a local temperature rise in the light-emitting device. The thickness of a substrate using a metal material or an alloy material is preferably greater than or equal to 10 µm and less than or equal to 200 µm, further preferably greater than or equal to 20 µm and less than or equal to 50 µm.

Although there is no particular limitation on a material for the metal substrate and the alloy substrate, it is preferable to use, for example, aluminum, copper, nickel, or a metal alloy such as an aluminum alloy or stainless steel.

Furthermore, when a material with high thermal emissivity is used for the substrate, the surface temperature of the light-emitting device can be prevented from rising, leading to prevention of breakage or a decrease in reliability of the light-emitting device. For example, the substrate may have a stacked-layer structure of a metal substrate and a layer with high thermal emissivity (e.g., a layer formed using a metal oxide or a ceramic material).

Examples of a material having flexibility and a light-transmitting property include polyester resins such as polyethylene terephthalate (PET) and polyethylene naphthalate (PEN), a polyacrylonitrile resin, a polyimide resin, a polymethyl methacrylate resin, a polycarbonate (PC) resin, a polyethersulfone (PES) resin, a polyamide resin (e.g., nylon or aramid), a cycloolefin resin, a polystyrene resin, a polyamide imide resin, a polyvinyl chloride resin, and a polytetrafluoroethylene (PTFE) resin. In particular, a material with a low coefficient of linear expansion is preferred, and for example, a polyamide imide resin, a polyimide resin, a polyamide resin, or PET can be suitably used. It is also possible to use a substrate in which a fibrous body is impregnated with a resin (also referred to as prepreg) or a substrate whose coefficient of linear expansion is reduced by mixing an organic resin with an inorganic filler.

The flexible substrate may have a stacked-layer structure of a layer of any of the above-mentioned materials and a hard coat layer by which a surface of the device is protected from damage (e.g., a silicon nitride layer), a layer that can disperse pressure (e.g., an aramid resin layer), or the like.

The flexible substrate may be formed by stacking a plurality of layers. When a glass layer is used, a barrier property against water or oxygen can be improved and thus a reliable light-emitting device can be provided.

For example, it is possible to use a flexible substrate in which a glass layer, a bonding layer, and an organic resin layer are stacked from the side closer to a light-emitting element. The thickness of the glass layer is greater than or equal to 20 μm and less than or equal to 200 μm, preferably greater than or equal to 25 μm and less than or equal to 100 μm. With such a thickness, the glass layer can have both high flexibility and a high barrier property against water or oxygen. The thickness of the organic resin layer is greater than or equal to 10 μm and less than or equal to 200 μm, preferably greater than or equal to 20 μm and less than or equal to 50 μm. Providing such an organic resin layer, occurrence of a crack or a break in the glass layer can be suppressed and mechanical strength can be improved. With the substrate using such a composite material of a glass material and an organic resin, a flexible light-emitting device with high reliability can be provided.

For the bonding layer, various curable adhesives such as a photo curable adhesive (e.g., an ultraviolet curable adhesive), a reactive curable adhesive, a thermosetting adhesive, and an anaerobic adhesive can be used. Examples of these adhesives include an epoxy resin, an acrylic resin, a silicone resin, a phenol resin, a polyimide resin, an imide resin, a polyvinyl chloride (PVC) resin, a polyvinyl butyral (PVB) resin, and an ethylene vinyl acetate (EVA) resin. A material with low moisture permeability, such as an epoxy resin, is particularly preferred. Alternatively, a two-component resin may be used. An adhesive sheet or the like may be used.

Further, the resin may include a drying agent. For example, it is possible to use a substance that adsorbs moisture by chemical adsorption, such as oxide of an alkaline earth metal (e.g., calcium oxide or barium oxide). Alternatively, it is possible to use a substance that adsorbs moisture by physical adsorption, such as zeolite or silica gel. The drying agent is preferably included because it can prevent impurities such as moisture from entering the functional element, thereby improving the reliability of the light-emitting device.

When a filler with a high refractive index or a light scattering member is mixed into the resin, the efficiency of light extraction from the light-emitting element can be improved. For example, titanium oxide, barium oxide, zeolite, or zirconium can be used.

Insulating films highly resistant to moisture are preferably used as the first insulating layer 705 and the second insulating layer 715. Alternatively, the first insulating layer 705 and the second insulating layer 715 each preferably have a function of preventing diffusion of impurities to the light-emitting element.

Examples of the insulating film highly resistant to moisture include a film containing nitrogen and silicon (e.g., a silicon nitride film and a silicon nitride oxide film) and a film containing nitrogen and aluminum (e.g., an aluminum nitride film). Alternatively, a silicon oxide film, a silicon oxynitride film, an aluminum oxide film, or the like may be used.

For example, the moisture vapor transmission rate of the insulating film highly resistant to moisture is lower than or equal to $1\times10^{-5}$ [g/(m$^2$·day)], preferably lower than or equal to $1\times10^{-6}$ [g/(m$^2$·day)], further preferably lower than or equal to $1\times10^{-7}$ [g/(m$^2$·day)], still further preferably lower than or equal to $1\times10^{-8}$ [g/(m$^2$·day)].

In the light-emitting device, it is necessary that at least one of the first insulating layer 705 and the second insulating layer 715 transmit light emitted from the light-emitting element. One of the first insulating layer 705 and the second insulating layer 715, which transmits light emitted from the light-emitting element, preferably has higher average transmittance of light having a wavelength greater than or equal to 400 nm and less than or equal to 800 nm than the other.

There is no particular limitation on the structure of the transistors in the light-emitting device. For example, a forward staggered transistor or an inverted staggered transistor may be used. A top-gate transistor or a bottom-gate transistor may be used. There is no particular limitation on a semiconductor material used for the transistors, and silicon, germanium, or an organic semiconductor can be used, for example. Alternatively, an oxide semiconductor containing at least one of indium, gallium, and zinc (e.g., In—Ga—Zn-based metal oxide) may be used.

There is no particular limitation on the crystallinity of a semiconductor material used for the transistors, and an amorphous semiconductor or a semiconductor having crystallinity (a microcrystalline semiconductor, a polycrystalline semiconductor, a single crystal semiconductor, or a semiconductor partly including crystal regions) may be used. A semiconductor having crystallinity is preferably used, in which case deterioration of the transistor characteristics can be suppressed.

In one embodiment of the present invention, a c-axis aligned crystalline oxide semiconductor (CAAC-OS) is preferably used as a semiconductor material for the transistors. Unlike amorphous semiconductor, the CAAC-OS has few defect states, so that the reliability of the transistor can be improved. Moreover, since the CAAC-OS does not have a grain boundary, a stable and uniform film can be formed over a large area, and stress that is caused by bending a flexible light-emitting device does not easily make a crack in a CAAC-OS film.

A CAAC-OS is a crystalline oxide semiconductor having c-axis alignment of crystals in a direction substantially perpendicular to the film surface. It has been found that oxide semiconductors have a variety of crystal structures other than a single crystal structure. An example of such structures is a nano-crystal (nc) structure, which is an aggregate of nanoscale microcrystals. The crystallinity of a CAAC-OS structure is lower than that of a single crystal structure and higher than that of an nc structure.

For stable characteristics of the transistor, a base film is preferably provided. The base film can be formed with a single-layer structure or a stacked-layer structure using an inorganic insulating film such as a silicon oxide film, a silicon nitride film, a silicon oxynitride film, or a silicon nitride oxide film. The base film can be formed by a sputtering method, a chemical vapor deposition (CVD) method (e.g., a plasma CVD method, a thermal CVD method, or a metal organic CVD (MOCVD) method), an atomic layer deposition (ALD) method, a coating method, a printing method, or the like. Note that the base film is not necessarily provided, in which the first insulating layer 705 can serve as a base film of the transistor.

As the light-emitting element, a self-luminous element can be used, and an element whose luminance is controlled by current or voltage is included in the category of the light-emitting element. For example, a light-emitting diode (LED), an organic EL element, or an inorganic EL element can be used.

The light-emitting element can have any of a top-emission structure, a bottom-emission structure, and a dual-emission structure. A conductive film that transmits visible light is used as the electrode through which light is extracted. A conductive film that reflects visible light is preferably used as the electrode through which light is not extracted.

The conductive film that transmits visible light can be formed using, for example, indium oxide, indium tin oxide (ITO), indium zinc oxide, zinc oxide (ZnO), or zinc oxide to which gallium is added. It is also possible to use a film of a metal material such as gold, silver, platinum, magnesium, nickel, tungsten, chromium, molybdenum, iron, cobalt, copper, palladium, or titanium; an alloy containing any of these metal materials; or a nitride of any of these metal materials (e.g., titanium nitride) when the film is thin enough to have a light-transmitting property. Alternatively, a stack of any of the above materials can be used as the conductive film. For example, a stacked film of ITO and an alloy of silver and magnesium is preferably used, in which case conductivity can be increased. Further alternatively, graphene or the like may be used.

For the conductive film that reflects visible light, a metal material such as aluminum, gold, platinum, silver, nickel, tungsten, chromium, molybdenum, iron, cobalt, copper, or palladium or an alloy containing any of these metal materials can be used, for example. Lanthanum, neodymium, germanium, or the like may be added to the metal material or the alloy. Moreover, the conductive film can be formed using an alloy containing aluminum (an aluminum alloy) such as an alloy of aluminum and titanium, an alloy of aluminum and nickel, an alloy of aluminum and neodymium, or an alloy of aluminum, nickel, and lanthanum (Al—Ni—La), or an alloy containing silver such as an alloy of silver and copper, an alloy of silver, palladium, and copper (Ag—Pd—Cu, also referred to as APC), or an alloy of silver and magnesium. An alloy of silver and copper is preferable because of its high heat resistance. When a metal film or a metal oxide film is stacked on an aluminum alloy film, oxidation of the aluminum alloy film can be suppressed. Examples of a material for the metal film or the metal oxide film are titanium and titanium oxide. Alternatively, the conductive film having a property of transmitting visible light and a film containing any of the above metal materials may be stacked. For example, it is possible to use a stacked film of silver and ITO or a stacked film of an alloy of silver and magnesium and ITO.

Each of the electrodes can be formed by an evaporation method or a sputtering method. Alternatively, a discharging method such as an ink-jet method, a printing method such as a screen printing method, or a plating method can be used.

When a voltage higher than the threshold voltage of the light-emitting element is applied between the lower electrode 831 and the upper electrode 835, holes are injected to the EL layer 833 from the anode side and electrons are injected to the EL layer 833 from the cathode side. The injected electrons and holes are recombined in the EL layer 833 and a light-emitting substance contained in the EL layer 833 emits light.

The EL layer 833 includes at least a light-emitting layer. In addition to the light-emitting layer, the EL layer 833 may further include one or more layers containing any of a substance with a high hole-injection property, a substance with a high hole-transport property, a hole-blocking material, a substance with a high electron-transport property, a substance with a high electron-injection property, a substance with a bipolar property (a substance with a high electron-transport property and a high hole-transport property), and the like.

For the EL layer 833, either a low molecular compound or a high molecular compound can be used, and an inorganic compound may be used. Each of the layers included in the EL layer 833 can be formed by any of the following methods: an evaporation method (including a vacuum evaporation method), a transfer method, a printing method, an ink-jet method, a coating method, and the like.

The light-emitting element 830 may contain two or more kinds of light-emitting substances. Thus, for example, a light-emitting element that emits white light can be achieved. For example, light-emitting substances are selected so that two or more light-emitting substances emit complementary colors to obtain white light emission. A light-emitting substance that emits red (R) light, green (G) light, blue (B) light, yellow (Y) light, or orange (O) light or a light-emitting substance that emits light containing spectral components of two or more of R light, G light, and B light can be used, for example. A light-emitting substance that emits blue light and a light-emitting substance that emits yellow light may be used, for example. At this time, the emission spectrum of the light-emitting substance that emits yellow light preferably contains spectral components of G light and R light. The emission spectrum of the light-emitting element 830 preferably has two or more peaks in the visible region (e.g., greater than or equal to 350 nm and less than or equal to 750 nm or greater than or equal to 400 nm and less than or equal to 800 nm).

The EL layer 833 may include a plurality of light-emitting layers. In the EL layer 833, the plurality of light-emitting layers may be stacked in contact with one another or may be stacked with a separation layer provided therebetween. The separation layer may be provided between a fluorescent layer and a phosphorescent layer, for example.

The separation layer can be provided, for example, to prevent energy transfer by the Dexter mechanism (particularly triplet energy transfer) from a phosphorescent material in an excited state which is generated in the phosphorescent layer to a fluorescent material in the fluorescent layer. The thickness of the separation layer is preferably several nanometers. Specifically, the thickness of the separation layer may be greater than or equal to 0.1 nm and less than or equal to 20 nm, greater than or equal to 1 nm and less than or equal to 10 nm, or greater than or equal to 1 nm and less than or equal to 5 nm. The separation layer contains a single material (preferably, a bipolar substance) or a plurality of materials (preferably, a hole-transport material and an electron-transport material).

The separation layer may be formed using a material contained in the light-emitting layer in contact with the separation layer. This facilitates the manufacture of the light-emitting element and reduces the drive voltage. For example, in the case where the phosphorescent layer contains a host material, an assist material, and the phosphorescent material (a guest material), the separation layer may contain the host material and the assist material. In other words, the separation layer includes a region not containing the phosphorescent material and the phosphorescent layer includes a region containing the phosphorescent material in the above structure. Thus, the separation layer and the phosphorescent layer can be separately deposited depending on the presence of the phosphorescent material. With such a structure, the separation layer and the phosphorescent layer can be formed in the same chamber. Thus, the manufacturing cost can be reduced.

Moreover, the light-emitting element 830 may be a single element including one EL layer or a tandem element in which EL layers are stacked with a charge generation layer provided therebetween.

The light-emitting element is preferably provided between a pair of insulating films that are highly resistant to moisture, in which case impurities such as water can be prevented from entering the light-emitting element, thereby preventing a decrease in the reliability of the light-emitting device. Specifically, the use of an insulating film highly resistant to moisture for the first insulating layer 705 and the second insulating layer 715 allows the light-emitting element to be located between a pair of insulating films highly resistant to moisture, by which a decrease in the reliability of the light-emitting device can be prevented.

As the insulating layer 815, an inorganic insulating film such as a silicon oxide film, a silicon oxynitride film, or an aluminum oxide film can be used, for example. For the insulating layers 817, 817a, and 817b, an organic material such as polyimide, acrylic, polyamide, polyimide amide, or a benzocyclobutene-based resin can be used, for example. Alternatively, a low dielectric constant material (low-k material) or the like can be used. Furthermore, each of the insulating layers may be formed by stacking a plurality of insulating films.

The insulating layer 821 is formed using an organic insulating material or an inorganic insulating material. As a resin, a polyimide resin, a polyamide resin, an acrylic resin, a siloxane resin, an epoxy resin, or a phenol resin can be used, for example. It is particularly preferable that the insulating layer 821 be formed using a photosensitive resin material to have an opening portion over the lower electrode 831 so that a sidewall of the opening portion is formed as an inclined surface with continuous curvature.

There is no particular limitation on the method for forming the insulating layer 821. For example, a photolithography method, a sputtering method, an evaporation method, a droplet discharging method (e.g., an ink-jet method), or a printing method (e.g., screen printing or off-set printing) may be used.

The spacer 823 can be formed using an inorganic insulating material, an organic insulating material, a metal material, or the like. As the inorganic insulating material and the organic insulating material, a variety of materials that can be used for the aforementioned insulating layers can be used, for example. As the metal material, titanium, aluminum, or the like can be used. When the spacer 823 containing a conductive material and the upper electrode 835 are electrically connected to each other, a potential drop due to the resistance of the upper electrode 835 can be suppressed. The spacer 823 may have a tapered shape or an inverse tapered shape.

A conductive layer functioning as an electrode of the transistor, a wiring, an auxiliary wiring of the light-emitting element, or the like in the light-emitting device can be formed with a single-layer structure or a stacked-layer structure using any of metal materials such as molybdenum, titanium, chromium, tantalum, tungsten, aluminum, copper, neodymium, and scandium and an alloy material containing any of these elements, for example. The conductive layer may be formed using a conductive metal oxide such as indium oxide (e.g., $In_2O_3$), tin oxide (e.g., $SnO_2$), ZnO, ITO, indium zinc oxide (e.g., $In_2O_3$—ZnO), or any of these metal oxide materials containing silicon oxide.

The coloring layer is a colored layer that transmits light in a specific wavelength range. For example, a color filter for transmitting light in a red, green, blue, or yellow wavelength range can be used. Each coloring layer is formed in a desired position with any of various materials by a printing method, an ink-jet method, an etching method using a photolithography method, or the like. In a white subpixel, a resin such as a transparent resin may be provided so as to overlap with the light-emitting element.

The light-blocking layer is provided between adjacent coloring layers. The light-blocking layer blocks light emitted from an adjacent light-emitting element to prevent color mixture between adjacent light-emitting elements. Here, the coloring layer is provided such that its end portion overlaps with the light-blocking layer, whereby light leakage can be reduced. For the light-blocking layer, a material that blocks light from the light-emitting element can be used; for example, a black matrix can be formed using a metal material or a resin material containing pigment or dye. Note that it is preferable to provide the light-blocking layer in a region other than the light-emitting portion, such as a driver circuit portion, in which case undesired leakage of guided light or the like can be suppressed.

An overcoat covering the coloring layer and the light-blocking layer may be provided. The overcoat can prevent impurities and the like contained in the coloring layer from being diffused into the light-emitting element. The overcoat is formed with a material that transmits light emitted from the light-emitting element; for example, it is possible to use an inorganic insulating film such as a silicon nitride film or a silicon oxide film, an organic insulating film such as an acrylic film or a polyimide film, or a stacked layer of an organic insulating film and an inorganic insulating film.

In the case where upper surfaces of the coloring layer and the light-blocking layer are coated with a material of the bonding layer, a material that has high wettability with respect to the material of the bonding layer is preferably used as the material of the overcoat. For example, the overcoat is preferably an oxide conductive film such as an ITO film or a metal film such as an Ag film that is thin enough to transmit light.

When the overcoat is formed using a material that has high wettability with respect to the material for the bonding layer, the material for the bonding layer can be uniformly applied. Thus, entry of bubbles in the step of attaching the pair of substrates to each other can be prevented, and thus a display defect can be prevented.

For the connector, any of a variety of anisotropic conductive films (ACF), anisotropic conductive pastes (ACP), and the like can be used.

Note that the light-emitting device of one embodiment of the present invention may be used as a display device or as a lighting device. For example, it may be used as a light source such as a backlight or a front light, that is, a lighting device for a display device.

This embodiment can be combined with any of the other embodiments as appropriate.

(Embodiment 3)

In this embodiment, a touch panel which is an input/output device of one embodiment of the present invention will be described. Note that the above description can be referred to for the components of a touch panel, which are similar to those of the light-emitting device described in Embodiment 2. Although a touch panel including a light-emitting element is described in this embodiment as an example, one embodiment of the present invention is not limited to this example.

The input/output device of one embodiment of the present invention can provide a strong or natural stereoscopic effect in a two-dimensional image. Furthermore, the input/output device of one embodiment of the present invention can provide a strong or natural stereoscopic effect in a two-dimensional image and is less likely to make a viewer fatigued.

STRUCTURE EXAMPLE 1

Figure 10A:
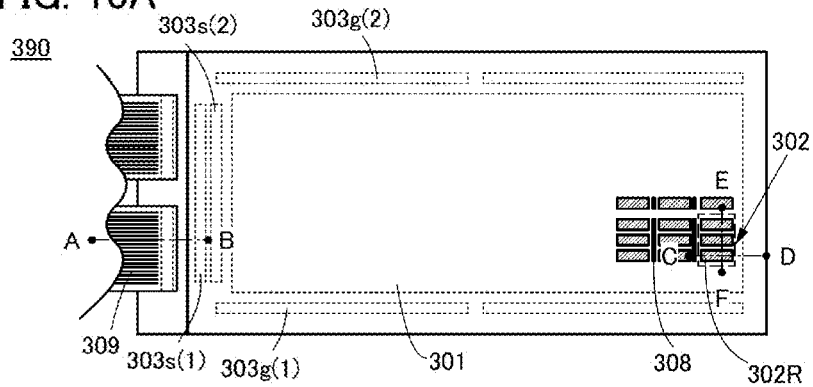
FIGS. 10A to 10C illustrate an example of an input/output device.
Figure 10B:
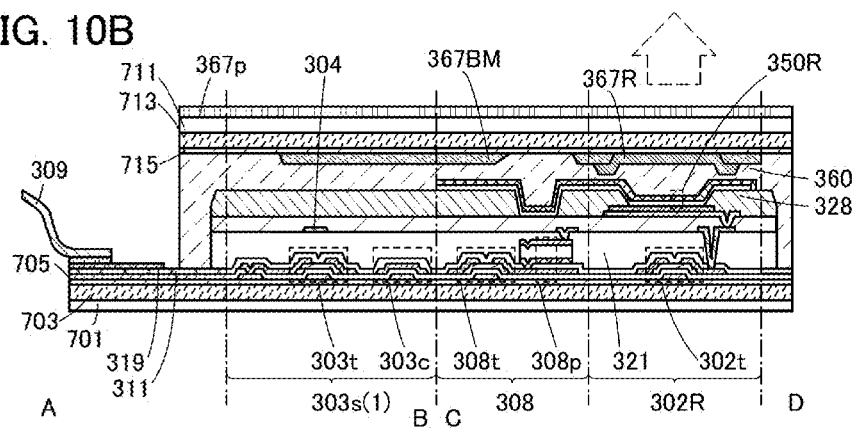
Figure 10C:
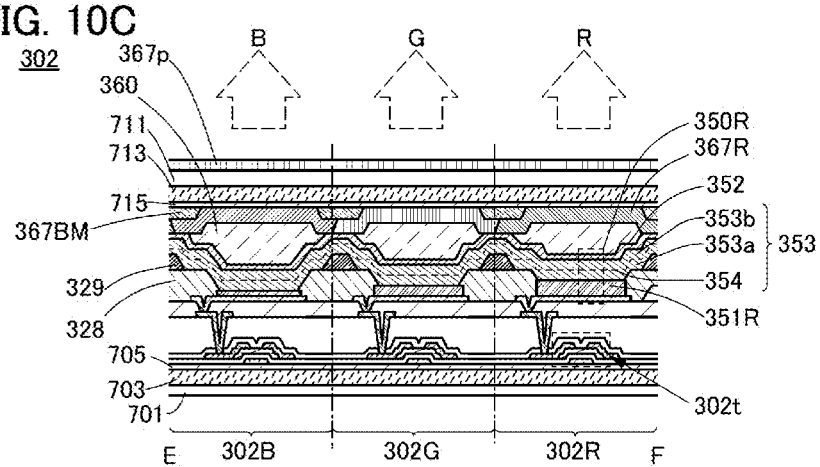

FIG. 10A is a top view of the input/output device. FIG. 10B is a cross-sectional view taken along dashed-dotted line A-B and dashed-dotted line C-D in FIG. 10A. FIG. 10C is a cross-sectional view taken along dashed-dotted line E-F in FIG. 10A.

A touch panel 390 illustrated in FIG. 10A includes a display portion 301 (serving also as an input portion), a scan line driver circuit 303g(1), an imaging pixel driver circuit 303g(2), an image signal line driver circuit 303s(1), and an imaging signal line driver circuit 303s(2).

The display portion 301 includes a plurality of pixels 302 and a plurality of imaging pixels 308.

The pixel 302 includes a plurality of subpixels. Each subpixel includes a light-emitting element and a pixel circuit.

The pixel circuits can supply electric power for driving the light-emitting element. The pixel circuits are electrically connected to wirings through which selection signals are supplied. The pixel circuits are also electrically connected to wirings through which image signals are supplied.

The scan line driver circuit 303g(1) can supply selection signals to the pixels 302.

The image signal line driver circuit 303s(1) can supply image signals to the pixels 302.

A touch sensor can be formed using the imaging pixels 308. Specifically, the imaging pixels 308 can sense a touch of a finger or the like on the display portion 301.

The imaging pixels 308 include photoelectric conversion elements and imaging pixel circuits.

The imaging pixel circuits can drive photoelectric conversion elements. The imaging pixel circuits are electrically connected to wirings through which control signals are supplied. The imaging pixel circuits are also electrically connected to wirings through which power supply potentials are supplied.

Examples of the control signal include a signal for selecting an imaging pixel circuit from which a recorded imaging signal is read, a signal for initializing an imaging pixel circuit, and a signal for determining the time it takes for an imaging pixel circuit to sense light.

The imaging pixel driver circuit 303g(2) can supply control signals to the imaging pixels 308.

The imaging signal line driver circuit 303s(2) can read out imaging signals.

As illustrated in FIGS. 10B and 10C, the touch panel 390 includes the first flexible substrate 701, the first bonding layer 703, the first insulating layer 705, the second flexible substrate 711, the second bonding layer 713, and the second insulating layer 715. The first flexible substrate 701 and the second flexible substrate 711 are bonded to each other with a third bonding layer 360.

The first flexible substrate 701 and the first insulating layer 705 are attached to each other with the first bonding layer 703. The second flexible substrate 711 and the second insulating layer 715 are attached to each other with the second bonding layer 713. Embodiment 2 can be referred to for materials used for the substrates, the bonding layers, and the insulating layers.

Each of the pixels 302 includes a subpixel 302R, a subpixel 302G, and a subpixel 302B (see FIG. 10C).

For example, the subpixel 302R includes a light-emitting element 350R and the pixel circuit. The pixel circuit includes a transistor 302t that can supply electric power to the light-emitting element 350R. Furthermore, the subpixel 302R includes an optical element (e.g., a coloring layer 367R that transmits red light).

The light-emitting element 350R includes a lower electrode 351R, an EL layer 353, and an upper electrode 352, which are stacked in this order (see FIG. 10C).

The EL layer 353 includes a first EL layer 353a, an intermediate layer 354, and a second EL layer 353b, which are stacked in this order.

Note that a microcavity structure can be provided for the light-emitting element 350R so that light with a specific wavelength can be efficiently extracted. Specifically, an EL layer may be provided between a film that reflects visible light and a film that partly reflects and partly transmits visible light, which are provided so that light with a specific wavelength can be efficiently extracted.

For example, the subpixel 302R includes the third bonding layer 360 that is in contact with the light-emitting element 350R and the coloring layer 367R. The coloring layer 367R is positioned in a region overlapping with the light-emitting element 350R. Accordingly, part of light emitted from the light-emitting element 350R passes through the third bonding layer 360 and through the coloring layer 367R and is emitted to the outside of the subpixel 302R as indicated by an arrow in FIG. 10B or 10C.

The touch panel 390 includes a light-blocking layer 367BM. The light-blocking layer 367BM is provided so as to surround the coloring layer (e.g., the coloring layer 367R).

The touch panel 390 includes an anti-reflective layer 367p positioned in a region overlapping with the display portion 301. As the anti-reflective layer 367p, a circular polarizing plate can be used, for example.

The touch panel 390 includes an insulating layer 321. The insulating layer 321 covers the transistor 302t and the like. Note that the insulating layer 321 can be used as a layer for planarizing unevenness caused by the pixel circuits and the imaging pixel circuits. The transistor 302t is preferably covered with an insulating layer that can inhibit diffusion of impurities to the transistor 302t and the like.

The touch panel 390 includes a partition 328 that overlaps with an end portion of the lower electrode 351R. A spacer 329 that controls the distance between the first flexible substrate 701 and the second flexible substrate 711 is provided on the partition 328.

The image signal line driver circuit 303s(1) includes a transistor 303t and a capacitor 303c. Note that the driver circuit can be formed in the same process and over the same substrate as the pixel circuits. As illustrated in FIG. 10B, the transistor 303t may include a second gate 304 over the insulating layer 321. The second gate 304 may be electrically connected to a gate of the transistor 303t, or different potentials may be supplied to these gates. Alternatively, if necessary, the second gate 304 may be provided for the transistor 308t, the transistor 302t, or the like.

The imaging pixels 308 each include a photoelectric conversion element 308p and an imaging pixel circuit. The imaging pixel circuit can sense light received by the photoelectric conversion element 308p. The imaging pixel circuit includes the transistor 308t. For example, a PIN photodiode can be used as the photoelectric conversion element 308p.

The touch panel 390 includes a wiring 311 through which a signal is supplied. The wiring 311 is provided with a terminal 319. Note that an FPC 309 through which a signal such as an image signal or a synchronization signal is supplied is electrically connected to the terminal 319. Note that a printed wiring board (PWB) may be attached to the FPC 309.

Note that transistors such as the transistors 302t, 303t, and 308t can be formed in the same process. Alternatively, the transistors may be formed in different processes.

STRUCTURE EXAMPLE 2

Figure 11A:
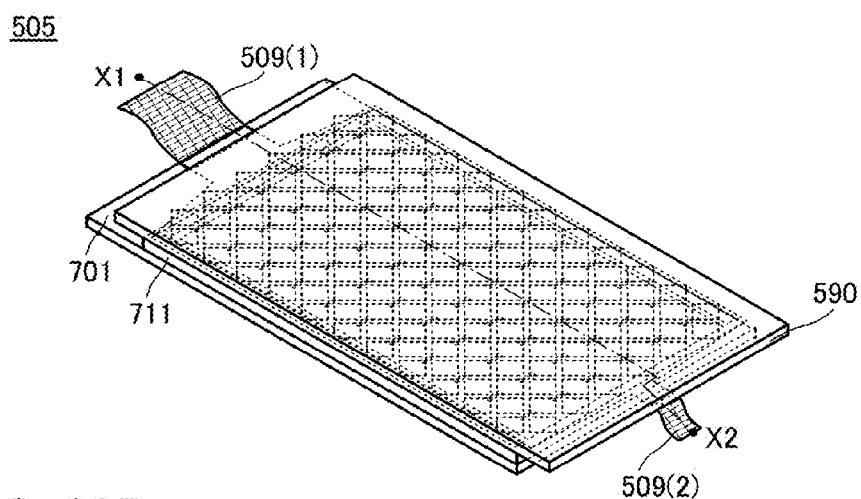
FIGS. 11A and 11B illustrate an example of an input/output device.
Figure 11B:
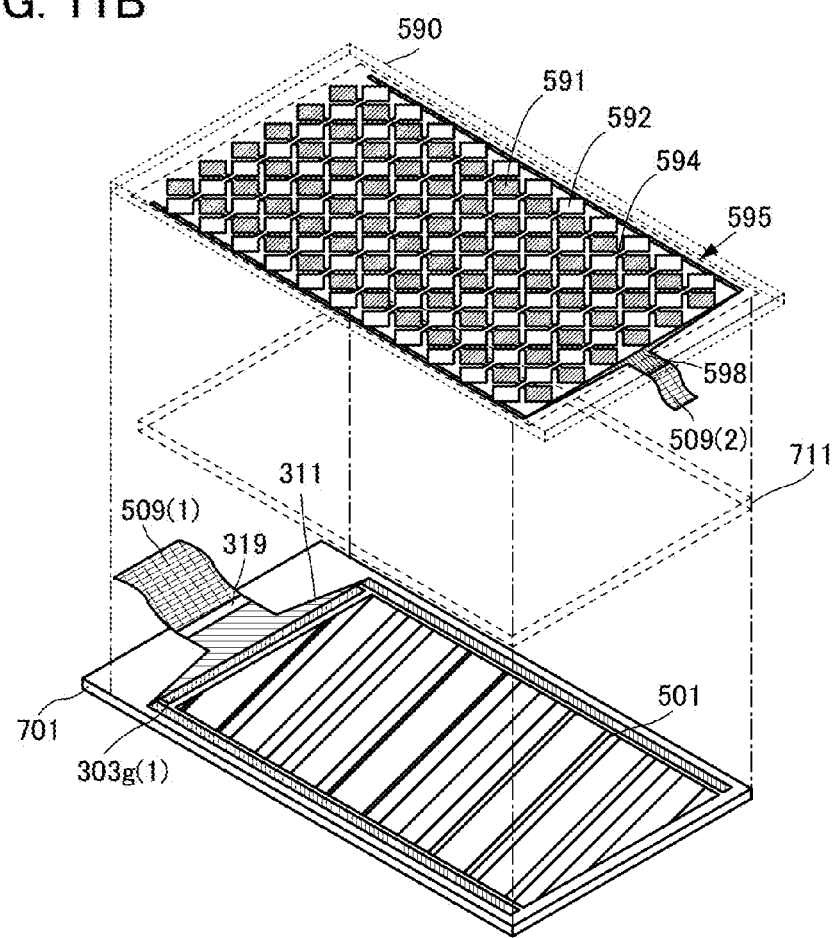
Figure 12A:
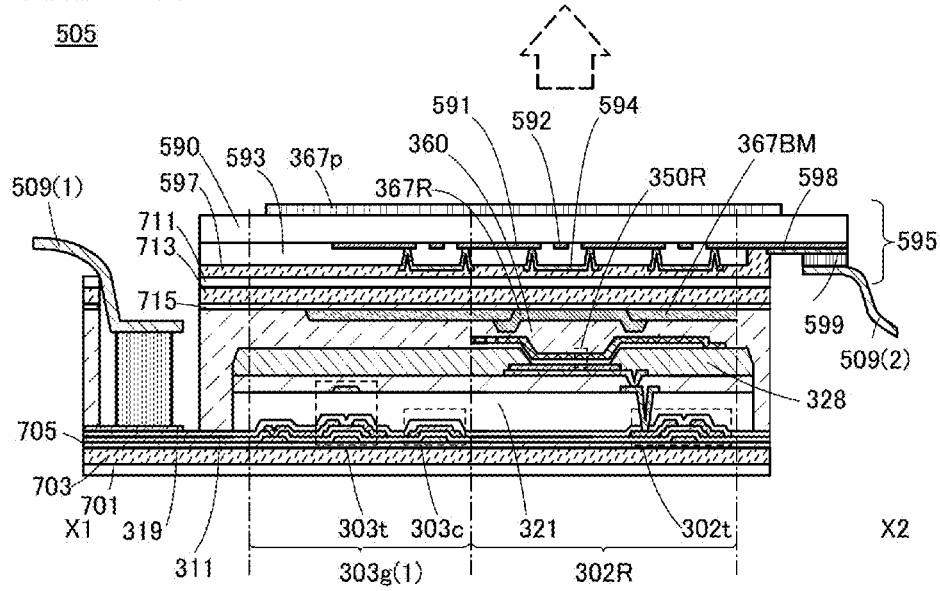
FIGS. 12A and 12B each illustrate an example of an input/output device.
Figure 12B:
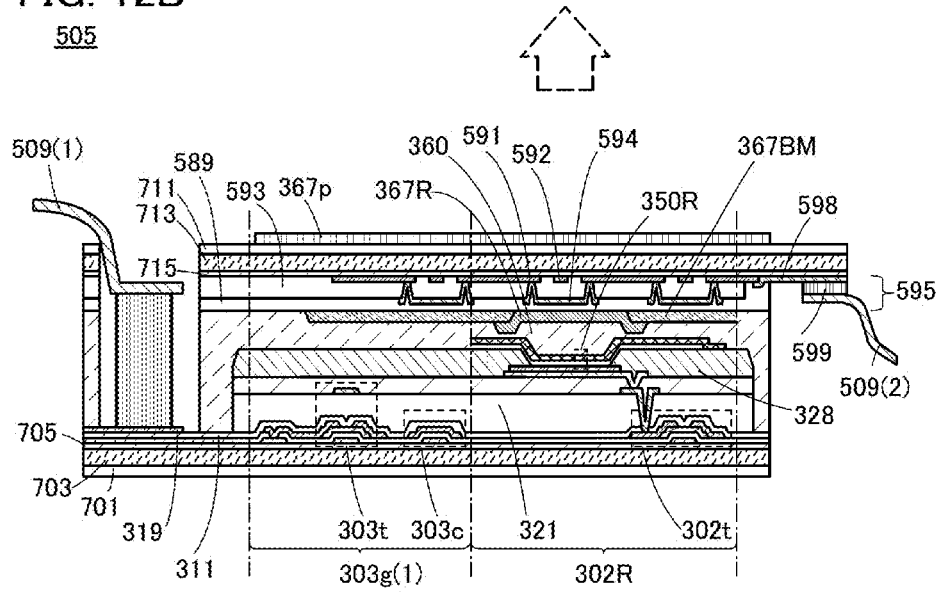

FIGS. 11A and 11B are perspective views of a touch panel 505. Note that FIGS. 11A and 11B illustrate only main components for simplicity. FIGS. 12A and 12B are each a cross-sectional view taken along dashed-dotted line X1-X2 in FIG. 11A.

As illustrated in FIGS. 11A and 11B, the touch panel 505 includes a display portion 501, the scan line driver circuit 303g(1), a touch sensor 595, and the like. Furthermore, the touch panel 505 includes the first flexible substrate 701, the second flexible substrate 711, and a flexible substrate 590.

The touch panel 505 includes a plurality of pixels and a plurality of wirings 311. The plurality of wirings 311 can supply signals to the pixels. The plurality of wirings 311 are arranged to a peripheral portion of the first flexible substrate 701, and part of the plurality of wirings 311 form the terminal 319. The terminal 319 is electrically connected to an FPC 509(1).

The touch panel 505 includes the touch sensor 595 and a plurality of wirings 598. The plurality of wirings 598 are electrically connected to the touch sensor 595. The plurality of wirings 598 are arranged to a peripheral portion of the flexible substrate 590, and part of the plurality of wirings 598 form a terminal The terminal is electrically connected to an FPC 509(2). Note that in FIG. 11B, electrodes, wirings, and the like of the touch sensor 595 provided on the back side of the flexible substrate 590 (the side facing the first flexible substrate 701) are indicated by solid lines for clarity.

As the touch sensor 595, for example, a capacitive touch sensor can be used. Examples of the capacitive touch sensor are a surface capacitive touch sensor and a projected capacitive touch sensor. An example of using a projected capacitive touch sensor is described here.

Examples of a projected capacitive touch sensor are a self-capacitive touch sensor and a mutual capacitive touch sensor. The use of a mutual capacitive type is preferable because multiple points can be sensed simultaneously.

Note that a variety of sensors that can sense the closeness or the contact of a sensing target such as a finger can be used as the touch sensor 595.

The projected capacitive touch sensor 595 includes electrodes 591 and electrodes 592. The electrodes 591 are electrically connected to any of the plurality of wirings 598, and the electrodes 592 are electrically connected to any of the other wirings 598.

The electrodes 592 each have a shape of a plurality of quadrangles arranged in one direction with one corner of a quadrangle connected to one corner of another quadrangle as illustrated in FIGS. 11A and 11B.

The electrodes 591 each have a quadrangular shape and are arranged in a direction intersecting with the direction in which the electrodes 592 extend. Note that the plurality of electrodes 591 are not necessarily arranged in the direction orthogonal to one electrode 592 and may be arranged to intersect with one electrode 592 at an angle of less than 90 degrees.

The wiring 594 intersects with the electrode 592. The wiring 594 electrically connects two electrodes 591 between which one of the electrodes 592 is positioned. The intersecting area of the electrode 592 and the wiring 594 is preferably as small as possible. Such a structure allows a reduction in the area of a region where the electrodes are not provided, reducing unevenness in transmittance. As a result, unevenness in luminance of light from the touch sensor 595 can be reduced.

Note that the shapes of the electrodes 591 and the electrodes 592 are not limited to the above-mentioned shapes and can be any of a variety of shapes.

As illustrated in FIG. 12A, the touch panel 505 includes the first flexible substrate 701, the first bonding layer 703, the first insulating layer 705, the second flexible substrate 711, the second bonding layer 713, and the second insulating layer 715. The first flexible substrate 701 and the second flexible substrate 711 are attached to each other with the third bonding layer 360.

A bonding layer 597 attaches the flexible substrate 590 to the second flexible substrate 711 so that the touch sensor 595 overlaps with the display portion 501. The bonding layer 597 has a light-transmitting property.

The electrodes 591 and the electrodes 592 are formed using a light-transmitting conductive material. As a light-transmitting conductive material, a conductive oxide such as indium oxide, indium tin oxide, indium zinc oxide, zinc oxide, or zinc oxide to which gallium is added can be used. Note that a film including graphene may be used as well. The film including graphene can be formed, for example, by reducing a film including graphene oxide. As a reducing method, a method with application of heat or the like can be employed.

Note that as a material of the conductive films such as the electrodes 591, the electrodes 592, and the wiring 594, that is, wirings and electrodes forming the touch panel, a transparent conductive film including indium oxide, tin oxide, zinc oxide, or the like (e.g., ITO) can be given. A low-resistance material is preferably used as a material that can be used as the wirings and electrodes forming the touch panel. For example, silver, copper, aluminum, a carbon nanotube, graphene, or a metal halide (such as a silver halide) may be used. Alternatively, a metal nanowire including a number of conductors with an extremely small width (for example, a diameter of several nanometers) may be used. Further alternatively, a net-like metal mesh with a conductor may be used. For example, an Ag nanowire, a Cu nanowire, an Al nanowire, an Ag mesh, a Cu mesh, or an Al mesh may be used. For example, in the case of using an Ag nanowire as the wirings and electrodes forming the touch panel, a visible light transmittance of 89% or more and a sheet resistance of 40 ohm/square or more and 100 ohm/square or less can be achieved. Since the above-described metal nanowire, metal mesh, carbon nanotube, graphene, and the like, which are examples of the material that can be used as the wirings and electrodes forming the touch panel, have high visible light transmittances, they may be used as electrodes of display elements (e.g., a pixel electrode or a common electrode).

The electrodes 591 and the electrodes 592 may be formed by depositing a light-transmitting conductive material on the flexible substrate 590 by a sputtering method and then removing an unnecessary portion by any of various patterning techniques such as photolithography.

The electrodes 591 and the electrodes 592 are covered with an insulating layer 593. Furthermore, openings reaching the electrodes 591 are formed in the insulating layer 593, and the wiring 594 electrically connects the adjacent electrodes 591. A light-transmitting conductive material can be favorably used for the wiring 594 because the aperture ratio of the touch panel can be increased. Moreover, a material with higher conductivity than the conductivities of the electrodes 591 and the electrodes 592 can be favorably used for the wiring 594 because electric resistance can be reduced.

Note that an insulating layer covering the insulating layer 593 and the wiring 594 may be provided to protect the touch sensor 595.

Furthermore, a connection layer 599 electrically connects the wirings 598 to the FPC 509(2).

The display portion 501 includes a plurality of pixels arranged in a matrix. Each pixel has the same structure as Structure Example 1; thus, description is omitted.

As illustrated in FIG. 12B, the touch panel may include two substrates of the first flexible substrate 701 and the second flexible substrate 711 without including the flexible substrate 590. The second flexible substrate 711 and the second insulating layer 715 are attached to each other with the second bonding layer 713, and the touch sensor 595 is provided in contact with the second insulating layer 715. The coloring layer 367R and the light-blocking layer 367BM are provided in contact with the insulating layer 589 that covers the touch sensor 595. The insulating layer 589 is not necessarily provided, in which case the coloring layer 367R or the light-blocking layer 367BM is provided in contact with the wiring 594.

STRUCTURE EXAMPLE 3

Figure 13A:
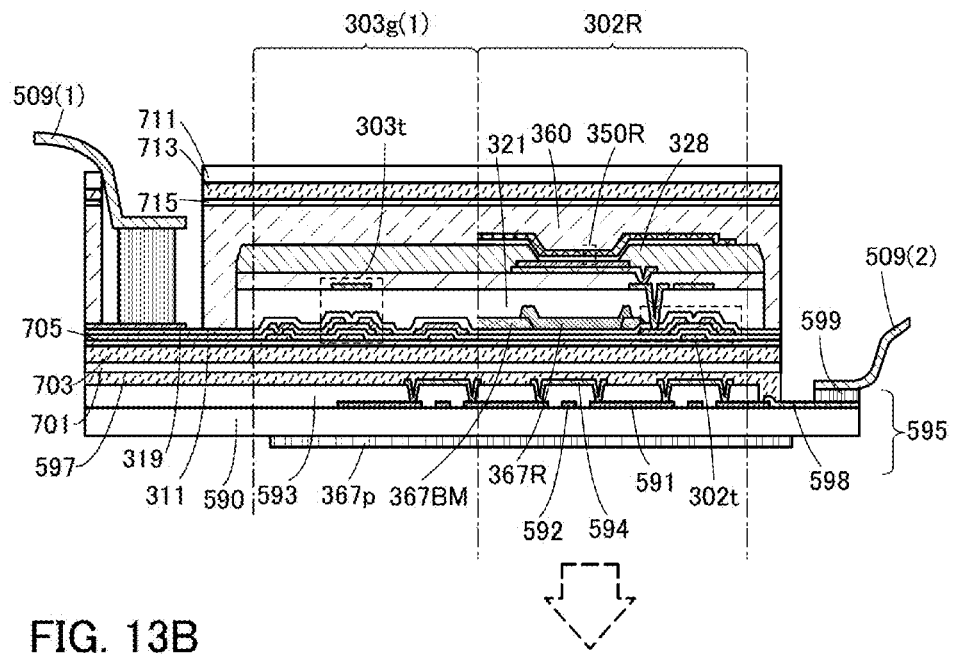
FIGS. 13A to 13C illustrate examples of an input/output device.
Figure 13B:
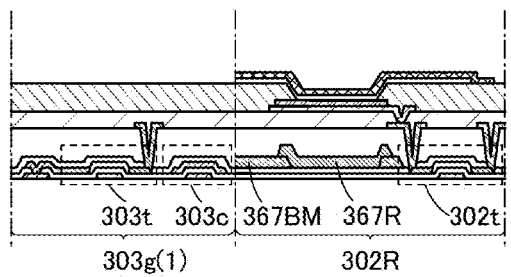
Figure 13C:
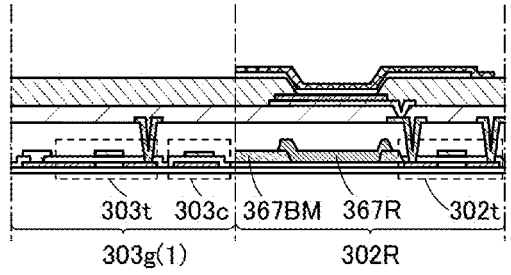

FIGS. 13A to 13C are cross-sectional views of a touch panel 505B. The touch panel 505B described in this embodiment is different from the touch panel 505 in Structure Example 2 in that received image data is displayed on the side where the transistors are provided and that the touch sensor is provided on the first flexible substrate 701 side of the display portion. Different structures will be described in detail below, and the above description is referred to for the other similar structures.

The coloring layer 367R is positioned in a region overlapping with the light-emitting element 350R. The light-emitting element 350R illustrated in FIG. 13A emits light to the side where the transistor 302t is provided. Accordingly, part of light emitted from the light-emitting element 350R passes through the coloring layer 367R and is emitted to the outside of the touch panel 505B as indicated by an arrow in FIG. 13A.

The touch panel 505B includes the light-blocking layer 367BM on the light extraction side. The light-blocking layer 367BM is provided so as to surround the coloring layer (e.g., the coloring layer 367R).

The touch sensor 595 is provided not on the second flexible substrate 711 side but on the first flexible substrate 701 side (see FIG. 13A).

The bonding layer 597 attaches the flexible substrate 590 to the first flexible substrate 701 so that the touch sensor 595 overlaps with the display portion. The bonding layer 597 has a light-transmitting property.

Note that a structure in the case of using bottom-gate transistors in the display portion 501 is illustrated in FIGS. 13A and 13B.

For example, a semiconductor layer containing an oxide semiconductor, amorphous silicon, or the like can be used in the transistor 302t and the transistor 303t illustrated in FIG. 13A.

For example, a semiconductor layer containing polycrystalline silicon or the like can be used in the transistor 302t and the transistor 303t illustrated in FIG. 13B.

A structure in the case of using top-gate transistors is illustrated in FIG. 13C.

For example, a semiconductor layer containing polycrystalline silicon, a single crystal silicon film that is transferred from a single crystal silicon substrate, or the like can be used in the transistor 302t and the transistor 303t illustrated in FIG. 13C.

This embodiment can be combined with any of the other embodiments as appropriate.

(Embodiment 4)

In this embodiment, electronic devices and lighting devices of one embodiment of the present invention will be described with reference to drawings.

With the use of a light-emitting device, a display device, an input/output device, or the like of one embodiment of the present invention, an electronic device or a lighting device with which a strong or natural stereoscopic effect can be obtained in a two-dimensional image can be fabricated. Furthermore, an electronic device or a lighting device with which a strong or natural stereoscopic effect can be obtained in a two-dimensional image and with which a user is less likely to be fatigued can be fabricated. One embodiment of the present invention can also be applied to an electronic device or a lighting device having a curved surface or flexibility.

Examples of electronic devices are a television set (also referred to as a television or a television receiver), a monitor of a computer or the like, a camera such as a digital camera or a digital video camera, a digital photo frame, a mobile phone handset (also referred to as a mobile phone or a mobile phone device), a goggle-type display (head mounted display), a portable game machine, a portable information terminal, an audio reproducing device, and a large-sized game machine such as a pachinko machine.

The electronic device or the lighting device of one embodiment of the present invention has flexibility and therefore can be incorporated along a curved inside/outside wall surface of a house or a building or a curved interior/exterior surface of a car.

Furthermore, the electronic device of one embodiment of the present invention may include a secondary battery. It is preferable that the secondary battery be capable of being charged by non-contact power transmission.

Examples of the secondary battery include a lithium ion secondary battery such as a lithium polymer battery using a gel electrolyte (lithium ion polymer battery), a nickel-hydride battery, a nickel-cadmium battery, an organic radical battery, a lead-acid battery, an air secondary battery, a nickel-zinc battery, and a silver-zinc battery.

The electronic device of one embodiment of the present invention may include an antenna. When a signal is received by the antenna, the electronic device can display an image, data, or the like on a display portion. When the electronic device includes the antenna and a secondary battery, the antenna may be used for contactless power transmission.

FIGS. 14A, 14B, 14C1, 14C2, 14D, and 14E illustrate examples of an electronic device including a display portion 7000 with a curved surface. The display surface of the display portion 7000 is curved, and images can be displayed on the curved display surface. The display portion 7000 may be flexible.

The display portion 7000 is formed using the light-emitting device, the display device, the input/output device, or the like of one embodiment of the present invention.

According to one embodiment of the present invention, an electronic device which includes a curved display portion and with which a strong or natural stereoscopic effect can be obtained in a two-dimensional image can be provided.

FIG. 14A illustrates an example of a mobile phone. A mobile phone 7100 includes a housing 7101, the display portion 7000, operation buttons 7103, an external connection port 7104, a speaker 7105, a microphone 7106, and the like.

The mobile phone 7100 illustrated in FIG. 14A includes a touch sensor in the display portion 7000. Operations such as making a call and inputting characters can be performed by touch on the display portion 7000 with a finger, a stylus, or the like.

The power can be turned on or off with the operation button 7103. In addition, types of images displayed on the display portion 7000 can be switched; for example, the image can be changed from a mail creation screen to a main menu.

FIG. 14B illustrates an example of a television set. In the television set 7200, the display portion 7000 is incorporated into the housing 7201. Here, the housing 7201 is supported by a stand 7203.

The television set 7200 illustrated in FIG. 14B can be operated with an operation switch of the housing 7201 or a separate remote controller 7211. The display portion 7000 may include a touch sensor. The television set 7200 can be operated by touching the display portion 7000 with a finger or the like. The remote controller 7211 may be provided with a display portion for displaying data output from the remote controller 7211. With operation keys or a touch panel of the remote controller 7211, channels or volume can be controlled and images displayed on the display portion 7000 can be controlled.

The television set 7200 is provided with a receiver, a modem, or the like. A general television broadcast can be received with the receiver. When the television set is connected to a communication network with or without wires via the modem, one-way (from a transmitter to a receiver) or two-way (between a transmitter and a receiver or between receivers) data communication can be performed.

FIGS. 14C1, 14C2, 14D, and 14E illustrate examples of a portable information terminal Each of the portable information terminals includes a housing 7301 and the display portion 7000. Each of the portable information terminals may also include an operation button, an external connection port, a speaker, a microphone, an antenna, a battery, or the like. The display portion 7000 is provided with a touch sensor. An operation of the portable information terminal can be performed by touching the display portion 7000 with a finger, a stylus, or the like.

FIG. 14C1 is a perspective view of a portable information terminal 7300. FIG. 14C2 is a top view of the portable information terminal 7300. FIG. 14D is a perspective view of a portable information terminal 7310. FIG. 14E is a perspective view of a portable information terminal 7320.

Each of the portable information terminals illustrated in this embodiment functions as, for example, one or more of a telephone set, a notebook, and an information browsing system. Specifically, the portable information terminals each can be used as a smartphone. Each of the portable information terminals described in this embodiment is capable of executing a variety of applications such as mobile phone calls, e-mailing, reading and editing texts, music reproduction, Internet communication, and a computer game, for example.

The portable information terminals 7300, 7310, and 7320 can display characters or image data on its plurality of surfaces. For example, as illustrated in FIGS. 14C1 and 14D, three operation buttons 7302 can be displayed on one surface, and data 7303 indicated by a rectangle can be displayed on another surface. FIGS. 14C1 and 14C2 illustrate an example in which data is displayed at the top of the portable information terminal. FIG. 14D illustrates an example in which data is displayed on the side of the portable information terminal Data may be displayed on three or more surfaces of the portable information terminal FIG. 14E illustrates an example where data 7304, data 7305, and data 7306 are displayed on different surfaces.

Examples of the data include notification from a social networking service (SNS), display indicating reception of e-mail or an incoming call, the title of e-mail or the like, the sender of e-mail or the like, the date, the time, remaining battery, the reception strength of an antenna, and the like. Instead of the data, an operation button, an icon, or the like may be displayed on the position where the data is displayed.

For example, a user of the portable information terminal 7300 can see the display (here, the data 7303) with the portable information terminal 7300 put in a breast pocket of his/her clothes.

Specifically, a caller's phone number, name, or the like of an incoming call is displayed in a position that can be seen from above the portable information terminal 7300. Thus, the user can see the display without taking out the portable information terminal 7300 from the pocket and decide whether to answer the call.

FIGS. 14F to 14H each illustrate an example of a lighting device having a curved light-emitting portion.

The light-emitting portion included in each of the lighting devices illustrated in FIGS. 14F to 14H can be manufactured using the light-emitting device or the like of one embodiment of the present invention.

According to one embodiment of the present invention, a lighting device having a curved light-emitting portion can be provided.

A lighting device 7400 illustrated in FIG. 14F includes a light-emitting portion 7402 having a wave-shaped light-emitting surface, which is a good-design lighting device.

A light-emitting portion 7412 included in the lighting device 7410 illustrated in FIG. 14G has two convex-curved light-emitting portions symmetrically placed. Thus, all directions can be illuminated with the lighting device 7410 as a center.

A lighting device 7420 illustrated in FIG. 14H includes a concave-curved light-emitting portion 7422. This is suitable for illuminating a specific range because light emitted from the light-emitting portion 7422 is collected to the front of the lighting device 7420. In addition, with this structure, a shadow is less likely to be produced.

The light-emitting portion included in each of the lighting devices 7400, 7410 and 7420 may be flexible. The light-emitting portion may be fixed on a plastic member, a movable frame, or the like so that an emission surface of the light-emitting portion can be curved freely depending on the intended use.

The lighting devices 7400, 7410, and 7420 each include a stage 7401 provided with an operation switch 7403 and a light-emitting portion supported by the stage 7401.

Note that although the lighting device in which the light-emitting portion is supported by the stage is described as an example here, a housing provided with a light-emitting portion can be fixed on a ceiling or suspended from a ceiling. Since the light-emitting surface can be curved, the light-emitting surface is curved to have a depressed shape, whereby a particular region can be brightly illuminated, or the light-emitting surface is curved to have a projecting shape, whereby a whole room can be brightly illuminated.

FIGS. 15A1, 15A2, and 15B to 15I illustrate examples of a portable information terminal including a display portion 7001 having flexibility.

The display portion 7001 is manufactured using the light-emitting device, the display device, the input/output device, or the like of one embodiment of the present invention. For example, a light-emitting device, a display device, or an input/output device that can be bent with a radius of curvature of greater than or equal to 0.01 mm and less than or equal to 150 mm can be used. The display portion 7001 may include a touch sensor so that the portable information terminal can be operated by touching the display portion 7001 with a finger or the like.

According to one embodiment of the present invention, an electronic device which includes a flexible display portion and with which a strong or natural stereoscopic effect can be obtained in a two-dimensional image can be provided.

FIG. 15A1 is a perspective view illustrating an example of a portable information terminal and FIG. 15A2 is a side view illustrating an example of the portable information terminal A portable information terminal 7500 includes a housing 7501, the display portion 7001, a display portion tab 7502, operation buttons 7503, and the like.

The portable information terminal 7500 includes a rolled flexible display portion 7001 in the housing 7501.

The portable information terminal 7500 can receive a video signal with a control portion incorporated therein and can display the received video on the display portion 7001. The portable information terminal 7500 incorporates a battery. A terminal portion for connecting a connector may be included in the housing 7501 so that a video signal or power can be directly supplied from the outside with a wiring.

By pressing the operation buttons 7503, power ON/OFF, switching of displayed videos, and the like can be performed. Although FIGS. 15A1, 15A2, and 15B illustrate an example where the operation buttons 7503 are positioned on a side surface of the portable information terminal 7500, one embodiment of the present invention is not limited thereto. The operation buttons 7503 may be placed on a display surface (a front surface) or a rear surface of the portable information terminal 7500.

FIG. 15B illustrates the portable information terminal 7500 in a state where the display portion 7001 is pulled out. Videos can be displayed on the display portion 7001 in this state. The display portion 7001 can be pulled out with the display portion tab 7502. In addition, the portable information terminal 7500 may perform different displays in the state where part of the display portion 7001 is rolled as shown in FIG. 15A1 and in the state where the display portion 7001 is pulled out as shown in FIG. 15B. For example, in the state shown in FIG. 15A1, the rolled portion of the display portion 7001 is put in a non-display state, which results in a reduction in power consumption of the portable information terminal 7500.

A reinforcement frame may be provided for a side portion of the display portion 7001 so that the display portion 7001 has a flat display surface when pulled out.

Note that in addition to this structure, a speaker may be provided for the housing so that sound is output with an audio signal received together with a video signal.

FIGS. 15C to 15E illustrate an example of a foldable portable information terminal FIG. 15C illustrates a portable information terminal 7600 that is opened. FIG. 15D illustrates the portable information terminal 7600 that is being opened or being folded. FIG. 15E illustrates the portable information terminal 7600 that is folded. The portable information terminal 7600 is highly portable when folded, and is highly browsable when opened because of a large seamless display area.

The display portion 7001 is supported by three housings 7601 joined together by hinges 7602. By folding the portable information terminal 7600 at a connection portion between two housings 7601 with the hinges 7602, the portable information terminal 7600 can be reversibly changed in shape from an opened state to a folded state.

FIGS. 15F and 15G illustrate an example of a foldable portable information terminal FIG. 15F illustrates a portable information terminal 7650 that is folded so that the display portion 7001 is on the inside. FIG. 15G illustrates the portable information terminal 7650 that is folded so that the display portion 7001 is on the outside. The portable information terminal 7650 includes the display portion 7001 and a non-display portion 7651. When the portable information terminal 7650 is not used, the portable information terminal 7650 is folded so that the display portion 7001 is on the inside, whereby the display portion 7001 can be prevented from being contaminated or damaged.

FIG. 15H illustrates an example of a flexible portable information terminal A portable information terminal 7700 includes a housing 7701 and the display portion 7001. The portable information terminal 7700 may include buttons 7703a and 7703b which serve as input means, speakers 7704a and 7704b which serve as sound output means, an external connection port 7705, a microphone 7706, or the like. A flexible battery 7709 can be mounted on the portable information terminal 7700. The battery 7709 may be arranged to overlap with the display portion 7001, for example.

The housing 7701, the display portion 7001, and the battery 7709 are flexible. Thus, it is easy to curve the portable information terminal 7700 into a desired shape or to twist the portable information terminal 7700. For example, the portable information terminal 7700 can be curved so that the display portion 7001 is on the inside or on the outside. The portable information terminal 7700 can be used in a rolled state. Since the housing 7701 and the display portion 7001 can be changed in shape freely in this manner, the portable information terminal 7700 is less likely to be broken even when the portable information terminal 7700 falls down or external stress is applied to the portable information terminal 7700.

The portable information terminal 7700 can be used effectively in various situations because the portable information terminal 7700 is lightweight. For example, the portable information terminal 7700 can be used in the state where the upper portion of the housing 7701 is suspended by a clip or the like, or in the state where the housing 7701 is fixed to a wall by magnets or the like.

FIG. 15I illustrates an example of a wrist-watch-type portable information terminal The portable information terminal 7800 includes a band 7801, the display portion 7001, an input/output terminal 7802, operation buttons 7803, and the like. The band 7801 has a function of a housing. A flexible battery 7805 can be mounted on the portable information terminal 7800. The battery 7805 may overlap with the display portion 7001 or the band 7801, for example.

The band 7801, the display portion 7001, and the battery 7805 have flexibility. Thus, the portable information terminal 7800 can be easily curved to have a desired shape.

With the operation buttons 7803, a variety of functions such as time setting, ON/OFF of the power, ON/OFF of wireless communication, setting and cancellation of silent mode, and setting and cancellation of power saving mode can be performed. For example, the functions of the operation button 7803 can be set freely by the operating system incorporated in the portable information terminal 7800.

By touching an icon 7804 displayed on the display portion 7001 with a finger or the like, application can be started.

The portable information terminal 7800 can employ near field communication that is a communication method based on an existing communication standard. In that case, for example, mutual communication between the portable information terminal 7800 and a headset capable of wireless communication can be performed, and thus hands-free calling is possible.

The portable information terminal 7800 may include the input/output terminal 7802. In the case where the input/output terminal 7802 is included, data can be directly transmitted to and received from another information terminal via a connector. Charging through the input/output terminal 7802 is also possible. Note that charging of the portable information terminal described as an example in this embodiment can be performed by non-contact power transmission without using the input/output terminal.

Figure 16A:
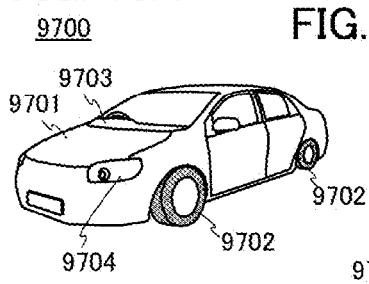
FIGS. 16A to 16C illustrate examples of an electronic device.
Figure 16B:
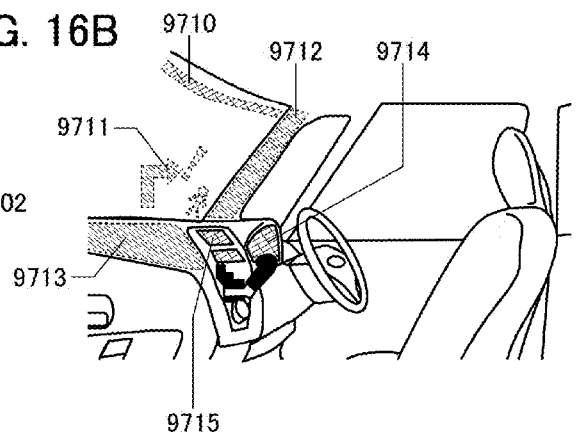

FIG. 16A is an external view of an automobile 9700. FIG. 16B illustrates a driver's seat of the automobile 9700. The automobile 9700 includes a car body 9701, wheels 9702, a dashboard 9703, lights 9704, and the like. The display device, the input/output device, or the like of one embodiment of the present invention can be used in a display portion or the like of the automobile 9700. For example, the display device, the input/output device, or the like of one embodiment of the present invention can be used in display portions 9710 to 9715 illustrated in FIG. 16B.

The display portion 9710 and the display portion 9711 are display devices provided in an automobile windshield. The display device, the input/output device, or the like of one embodiment of the present invention can be a see-through device, through which the opposite side can be seen, by using a light-transmitting conductive material for its electrodes and wirings. The see-through display portion 9710 and the see-through display portion 9711 do not hinder driver's vision during driving of the automobile 9700. Therefore, the display device, the input/output device, or the like of one embodiment of the present invention can be provided in the windshield of the automobile 9700. Note that in the case where a transistor or the like for driving the display device, the input/output device, or the like is provided, a transistor having a light-transmitting property, such as an organic transistor using an organic semiconductor material or a transistor using an oxide semiconductor, is preferably used.

The display portion 9712 is a display device provided on a pillar portion. For example, an image taken by an imaging unit provided in the car body is displayed on the display portion 9712, whereby the view hindered by the pillar portion can be compensated. The display portion 9713 is a display device provided on the dashboard. For example, an image taken by an imaging unit provided in the car body is displayed on the display portion 9713, whereby the view hindered by the dashboard can be compensated. That is, by displaying an image taken by an imaging unit provided on the outside of the automobile, blind areas can be eliminated and safety can be increased. Displaying an image to compensate for the area which a driver cannot see makes it possible for the driver to confirm safety easily and comfortably.

Figure 16C:
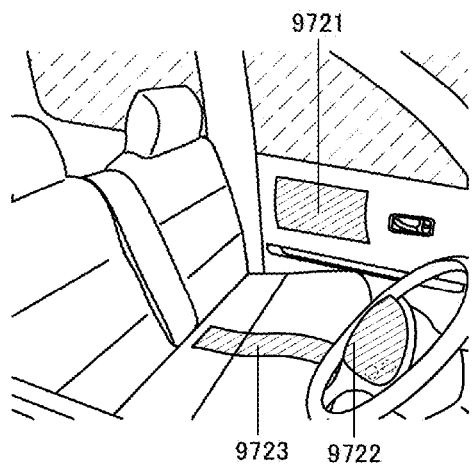

FIG. 16C illustrates the inside of a car in which bench seats are used for a driver seat and a front passenger seat. A display portion 9721 is a display device provided in a door portion. For example, an image taken by an imaging unit provided in the car body is displayed on the display portion 9721, whereby the view hindered by the door can be compensated. A display portion 9722 is a display device provided in a steering wheel. A display portion 9723 is a display device provided in the middle of a seating face of the bench seat. Note that the display device can be used as a seat heater by providing the display device on the seating face or backrest and by using heat generation of the display device as a heat source.

The display portion 9714, the display portion 9715, and the display portion 9722 can provide a variety of kinds of data such as navigation data, a speedometer, a tachometer, a mileage, a fuel meter, a gearshift indicator, and air-condition setting. The content, layout, and the like of the display on the display portions can be changed freely by a user as appropriate. The data listed above can also be displayed on the display portions 9710 to 9713, 9721, and 9723. The display portions 9710 to 9715 and 9721 to 9723 can also be used as lighting devices. The display portions 9710 to 9715 and 9721 to 9723 can also be used as heating devices.

This embodiment can be combined with any of the other embodiments as appropriate.

EXAMPLE 1

In this example, the results of sensitivity evaluation for examining the correlation between a stereoscopic effect that a viewer feels in a two-dimensional image displayed on a display portion, the size of the display portion, and the degree of curvature of the display portion will be described.

Three kinds of display devices were used for the sensitivity evaluation. Each of the display devices is a flexible organic EL display, and displays an image with a display portion curved.

As a light-emitting element, a tandem (stacked-layer) organic EL element emitting white light was used. The light-emitting element has a top-emission structure. Light from the light-emitting element is extracted to the outside of the organic EL display through a color filter. The luminance at the time of white display (daylight color (D65: $x=0.31$, $y=0.33$)) was 300 cd/m$^2$.

The display device of the first kind was a 3.4-inch organic EL display having a definition of 326 ppi and a resolution of QHD (quarter high definition, 960×540×RGB).

The display device of the second kind was a 5.9-inch organic EL display having a definition of 249 ppi and a resolution of HD (high definition, 1280×720×RGB).

The display device of the third kind was a 9.2-inch organic EL display having a definition of 238 ppi and a resolution of FHD (full high definition, 1920×1080×RGB).

In this example, two display devices of the same kind were used. One of them was used with a display portion curved, and the other was used in a flat state without a display portion curved as a comparative example.

The evaluation was performed in such a manner that viewers compared the display device having the curved display portion with the comparative display device having the flat display portion that were laid side by side.

The viewers compared a moving image displayed on the curved display portion with the same moving image displayed on the comparative flat display portion to evaluate whether there was a difference in "stereoscopic effect," "pop-out effect," "sense of depth," "tiredness," "naturalness," and "whether to want to actually use the sample as a device." Note that "pop-out effect" used as an evaluation term means that the viewer feels as if the moving image approaches the viewer. Furthermore, "sense of depth" means that the viewer feels as if there is a spread on the back side of the display portion. Note that "stereoscopic effect" includes the pop-out effect and the sense of depth, and is an evaluation term whose meaning is the closest to natural3D. Furthermore, "naturalness" means that there is no uncomfortable feeling.

For the evaluation, a semantic differential (SD) method was used. Specifically, the viewers rated "stereoscopic effect," "pop-out effect," "sense of depth," "tiredness," "naturalness," and "whether to want to actually use the sample as a device" in the case of the moving image displayed on the curved display portion on a 5-point scale (±2, ±1, and 0) in comparison with the same moving image displayed on the flat display portion. For example, "stereoscopic effect," "pop-out effect," and "sense of depth" were each rated on a 5-point scale ("too strong (+2)," "strong (+1)," "equal (0)," "weak (−1)," and "too weak (−2)." As for "tiredness," the positive values show that the viewer was less tired and the negative values show that the viewer was more tired.

The obtained results were subjected to a statistically-significant difference test to ensure the reliability of the experiments. Note that in all the experiments described in this example, the number of the subjects was 20 or more large enough for statistical evaluation. The specific number of the subjects for the 3.4-inch display panel was 28, that for the 5.9-inch display panel was 23, and that for the 9.2-inch display panel was 20. Note that the visual distance was 30 cm in all the conditions described in this example.

In this example, the display devices were each bent in the horizontal direction of the display portion (the long-axis direction of the display portion). How to bend the display device was divided into two types: some of the display devices were bent so as to have a convex surface (convex curved surface) on the display surface side (viewer side) as illustrated in FIG. 1A1 and FIGS. 17A to 17D, and the others were bent so as to have a concave surface (concave curved surface) on the display surface side (viewer side) as illustrated in FIG. 1B1 and FIGS. 17E to 17H. The central angle θ of the curved surface was approximately 21°, approximately 42°, approximately 85°, and approximately 140°. FIGS. 17A to 17H show the display devices which were each bent so as to have a convex or concave surface with a central angle of θ. Note that the relation between the central angle θ and the radius R of curvature in each of the display panels having the respective sizes is shown in Table 1.

TABLE 1

| Size | θ | R |
|---|---|---|
| 3.4 inches | approximately 21° | 200 mm |
| | approximately 42° | 100 mm |
| | approximately 85° | 50 mm |
| | approximately 140° | 30 mm |
| 5.9 inches | approximately 21° | 350 mm |
| | approximately 42° | 175 mm |
| | approximately 85° | 85 mm |
| | approximately 140° | 50 mm |
| 9.2 inches | approximately 21° | 540 mm |
| | approximately 42° | 270 mm |
| | approximately 85° | 135 mm |
| | approximately 140° | 80 mm |

FIGS. 18A and 18B, FIGS. 19A and 19B, FIGS. 20A and 20B, FIGS. 21A and 21B, FIGS. 22A and 22B, and FIGS. 23A and 23B show evaluation results. FIG. 18A, FIG. 19A, FIG. 20A, FIG. 21A, FIG. 22A, and FIG. 23A show the results on the convex surfaces, and FIG. 18B, FIG. 19B, FIG. 20B, FIG. 21B, FIG. 22B, and FIG. 23B show the results on the concave surfaces. In the evaluation results, the average score of all the subjects is shown. A condition under which a significant difference is statistically observed with a probability of 95% or more is indicated by *.

Figure 18A:
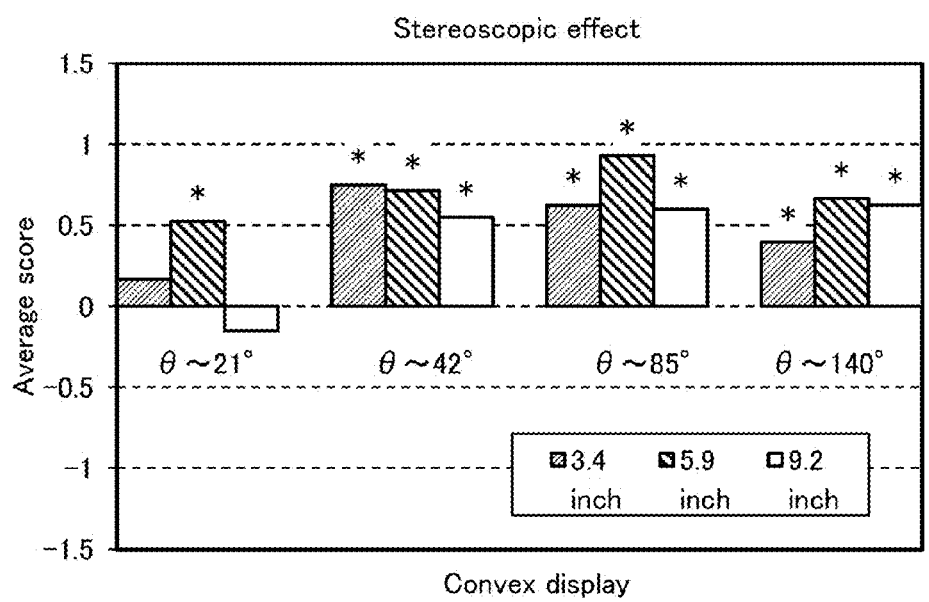
FIGS. 18A and 18B show sensitivity evaluation results in Example 1.
Figure 18B:
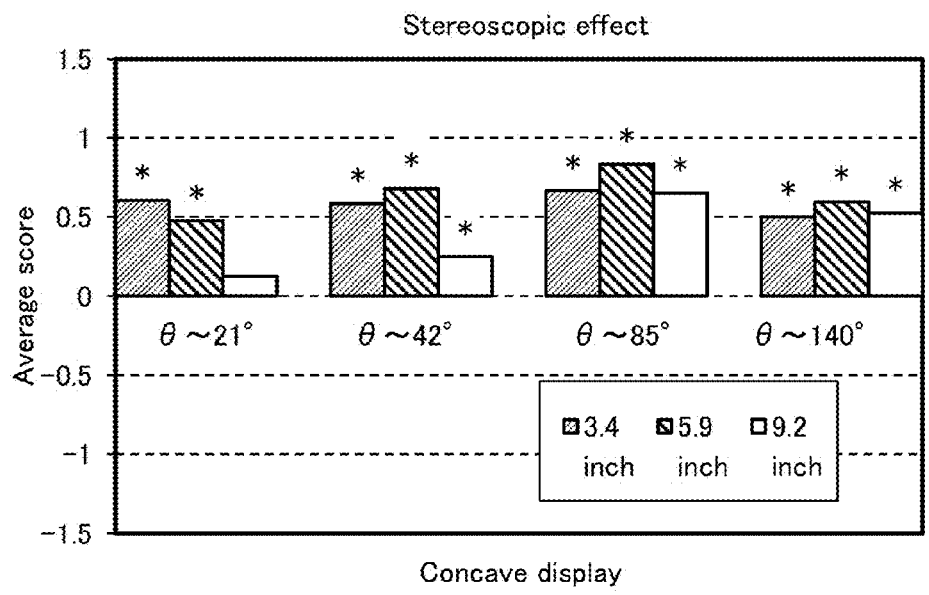
Figure 19A:
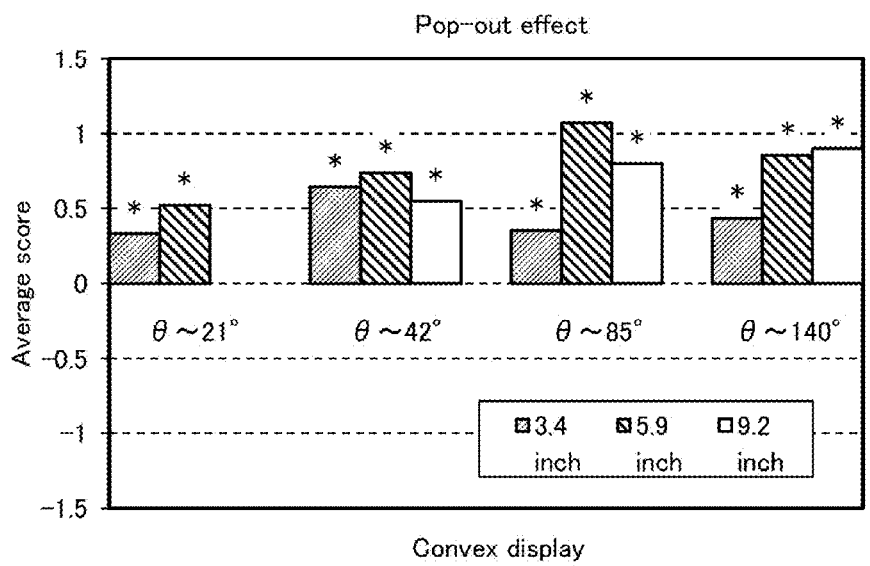
FIGS. 19A and 19B show sensitivity evaluation results in Example 1.
Figure 19B:
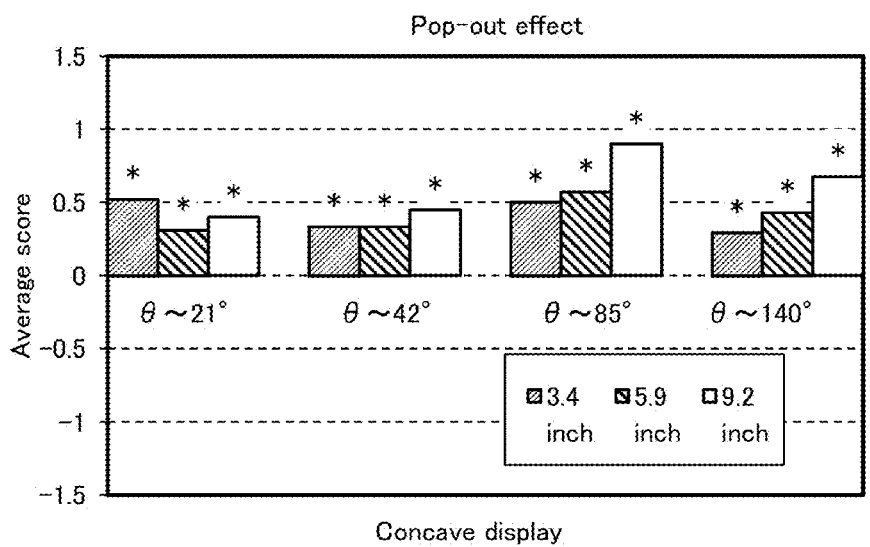
Figure 20A:
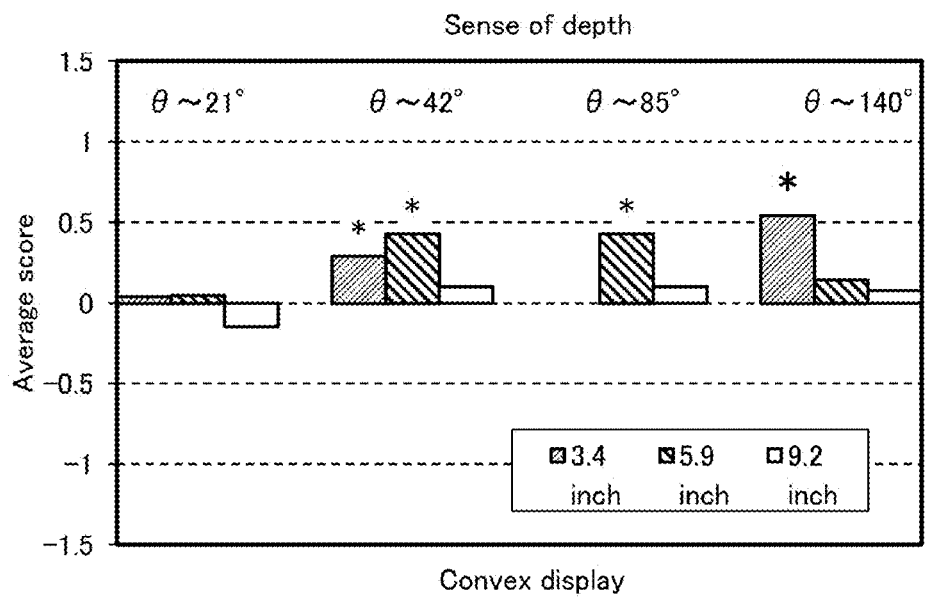
FIGS. 20A and 20B show sensitivity evaluation results in Example 1.
Figure 20B:
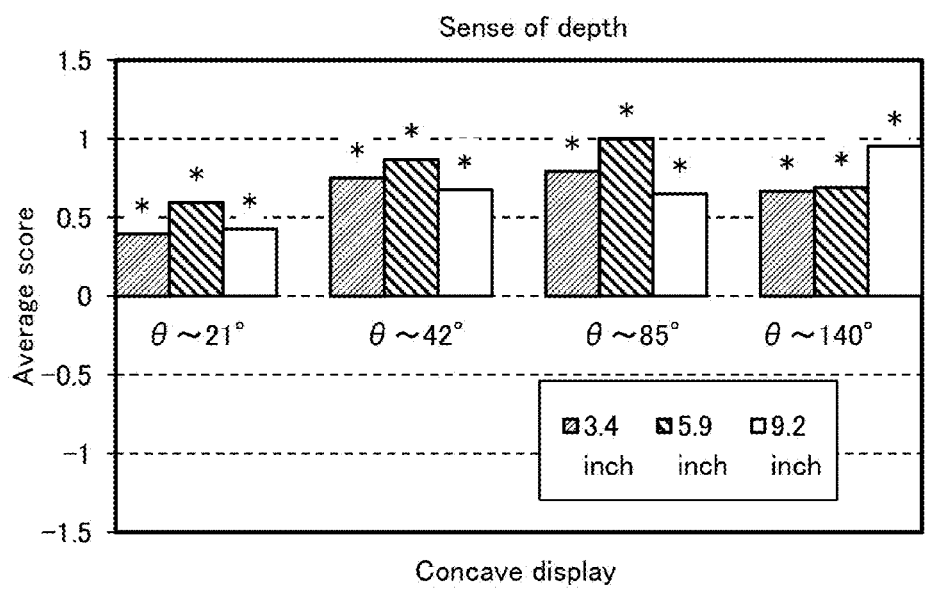
Figure 21A:
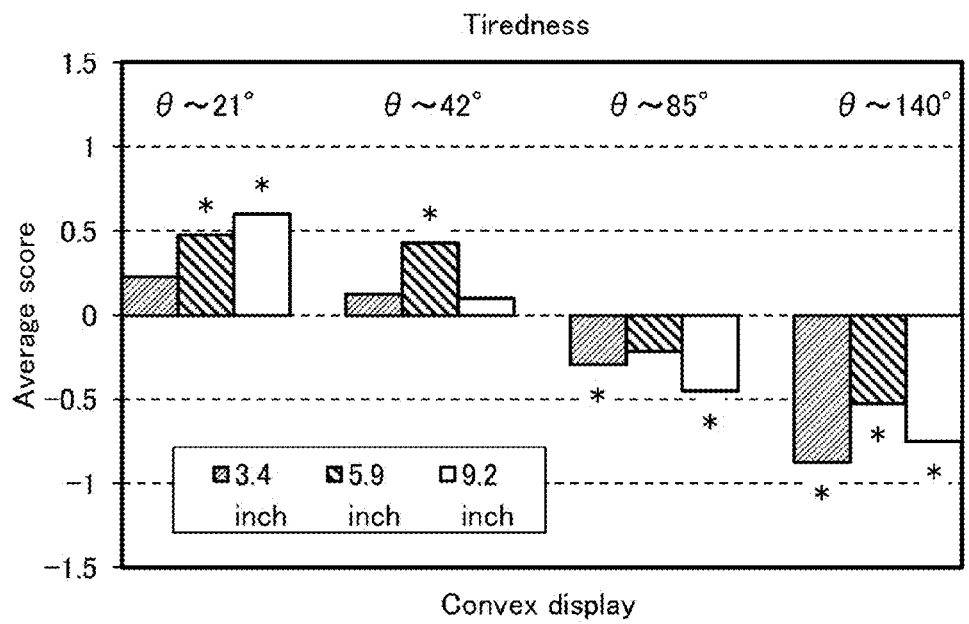
FIGS. 21A and 21B show sensitivity evaluation results in Example 1.
Figure 21B:
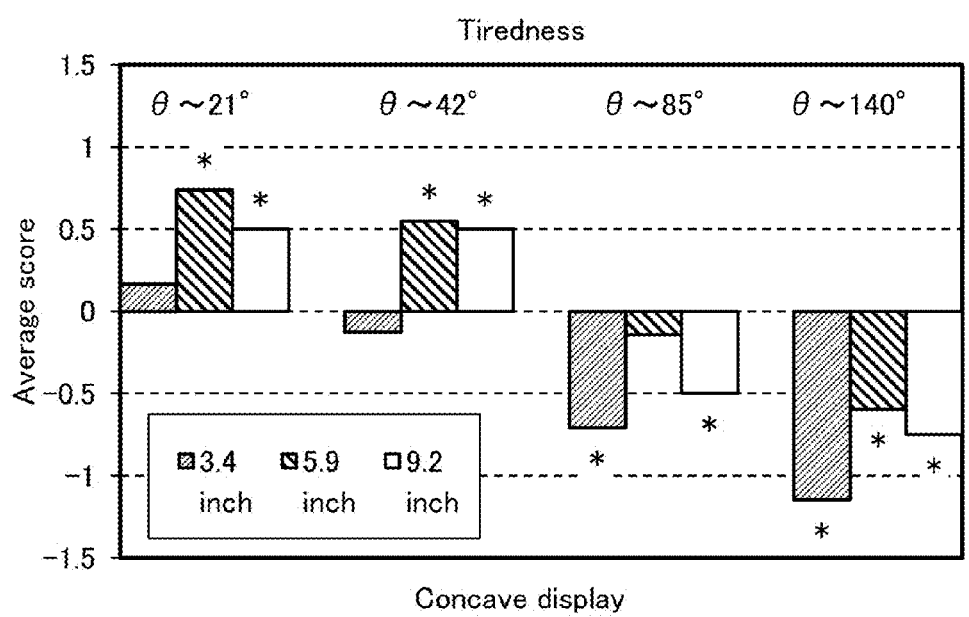
Figure 22A:
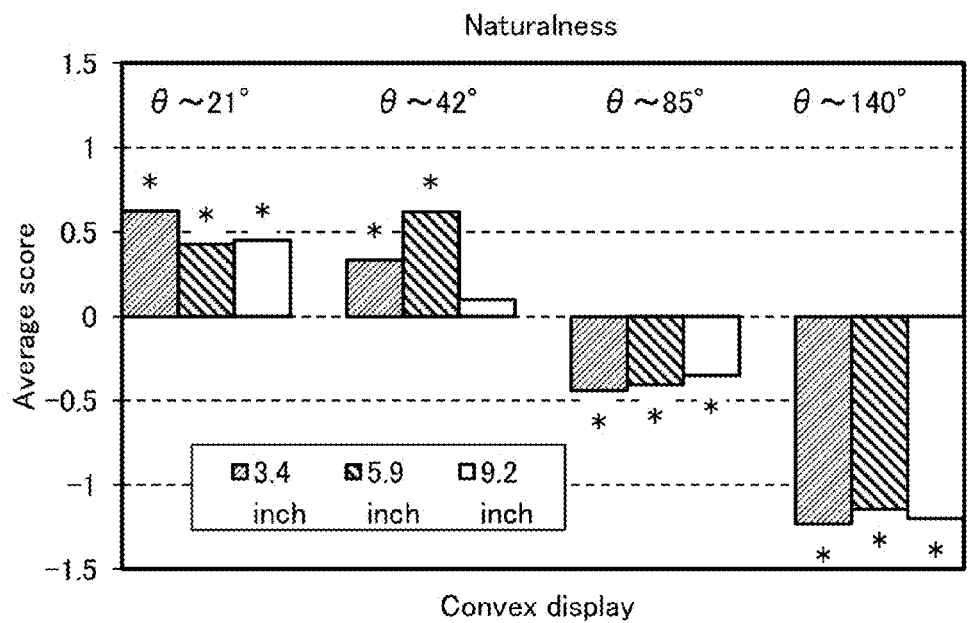
FIGS. 22A and 22B show sensitivity evaluation results in Example 1.
Figure 22B:
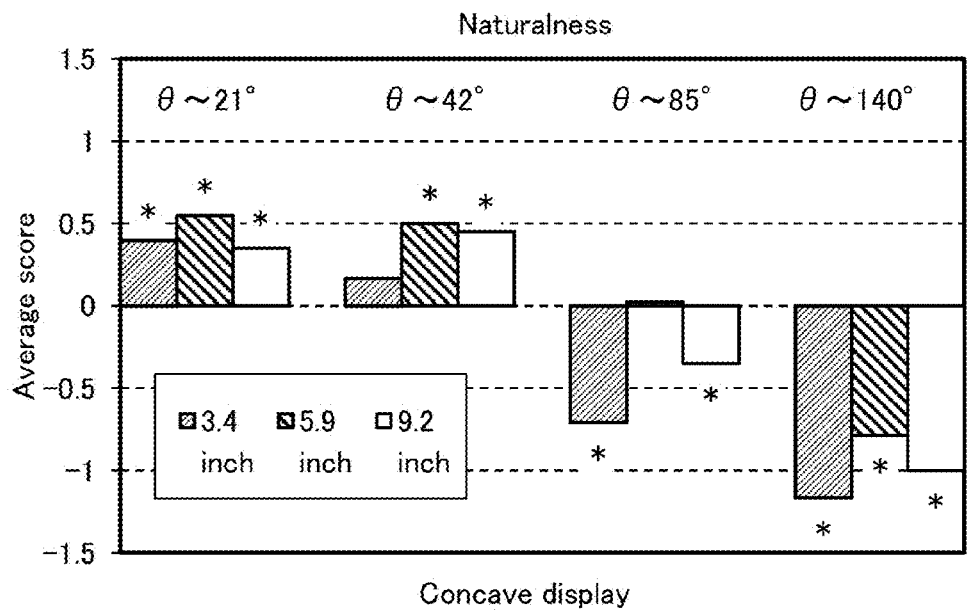
Figure 23A:
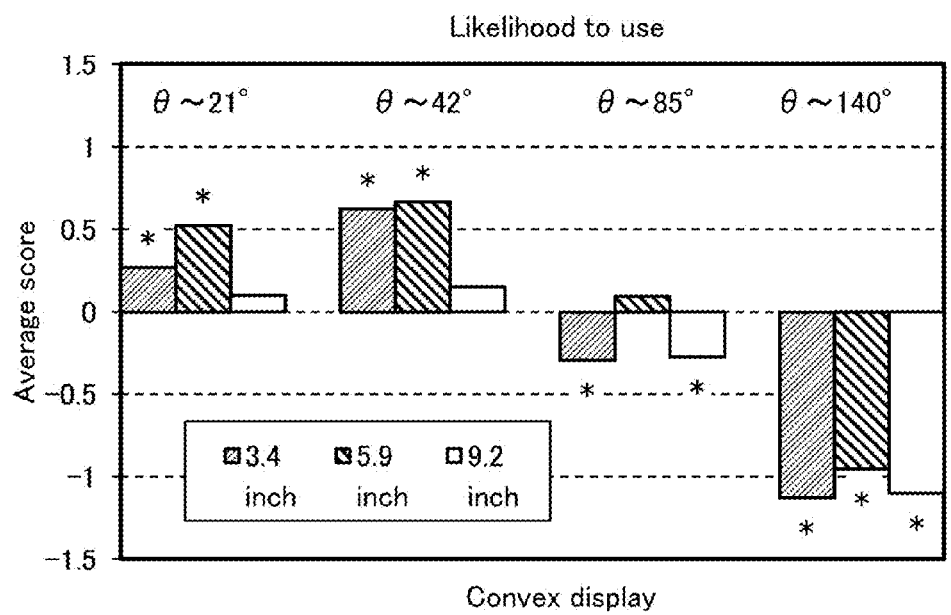
FIGS. 23A and 23B show sensitivity evaluation results in Example 1.
Figure 23B:
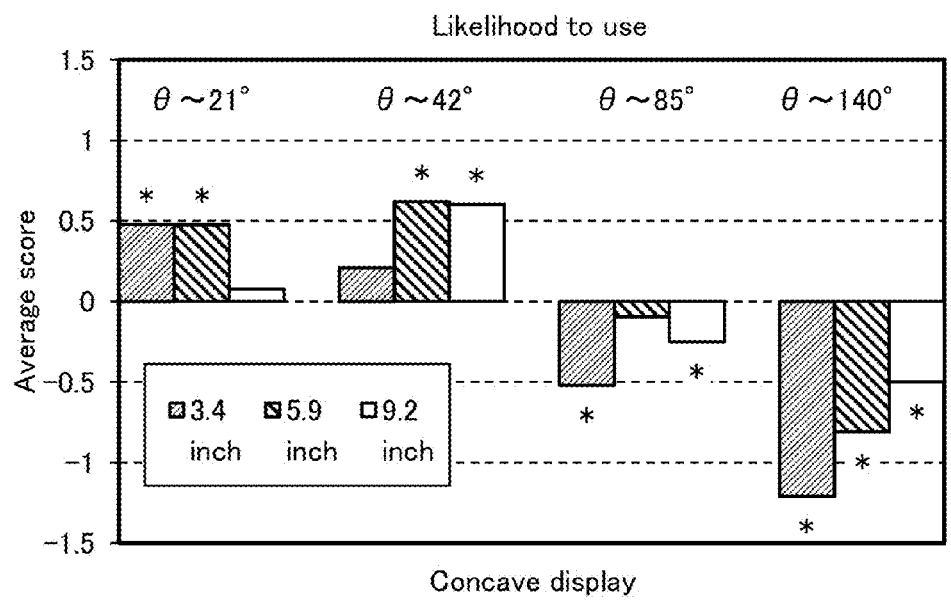

As shown in FIGS. 18A and 18B, the stereoscopic effect in the case of the curved display portion was stronger than that in the case of the comparative flat display portion under almost all the conditions, regardless of the size of the display portion, the central angle, and how to bend the display device.

As shown in FIGS. 19A and 19B and FIGS. 20A and 20B, the pop-out effect tended to be stronger particularly in the case where the display device was bent so as to have a convex surface, and the sense of depth tended to be stronger particularly in the case where the display device was bent so as to have a concave surface.

When the central angle θ was approximately 42°, approximately 85°, and approximately 140°, the stereoscopic effect, the pop-out effect, and the sense of depth tended to be stronger than when the central angle Bis approximately 21°.

The stereoscopic effect, the pop-out effect, and the sense of depth tended to be improved effectively when the size of the display panel was 3.4 inches and the central angle θ is approximately 42°, when those were 5.9 inches and approximately 85°, and when those were 9.2 inches and approximately 140°. These values are equivalent to a radius of curvature of approximately 100 mm. From the above, the size of a display portion is less likely to affect a radius of curvature at which a stereoscopic effect or the like can be effectively improved.

As shown in FIGS. 21A and 21B, FIGS. 22A and 22B, and FIGS. 23A and 23B, tiredness, naturalness, and whether to want to actually use the sample as a device show similar results.

Specifically, in the case where θ was approximately 21° and approximately 42°, the subjects tended to be less tired, feel less uncomfortable feeling, and want to use them actually as compared with the case where θ was approximately 85° and approximately 140°.

As a whole, when θ is approximately 42° or smaller, the subjects tended to see the moving image more naturally, to be less tired, and to want to use them actually than in the case of the flat display portions. In particular, in the case of the relatively large display device having a size of 5.9 inches or 9.2 inches, there was a statistically significant difference in tiredness. This is probably because the larger the display portion is, the less likely the viewing angle is to be narrow and the less likely strain on eyes or brain is to be caused.

From the above, the optimal central angle is approximately 42° under the conditions of this example, at which a natural stereoscopic effect can be obtained in a two-dimensional image and a viewer is less likely to be tired.

Note that a condition under which a strong stereoscopic effect is felt or less tiredness is caused varied between individuals. Therefore, it is found that not fixing the curvature of a display portion but changing the degree of the curvature of the display portion as appropriate is preferred like in the case of a display device or a display system of one embodiment of the present invention.

EXAMPLE 2

In this example, quantitative evaluation of stereoscopic effects that viewers felt will be described.

Before the evaluation of this example, the sensitive evaluation results showed that the contrast of an image is one of parameters by which a viewer can feel a stereoscopic effect in a two-dimensional image.

Furthermore, before the evaluation of this example, the intensity of stereoscopic effect that viewers felt in a two-dimensional image displayed on a 3.93-inch flat organic EL display (with a definition of 458 ppi and a contrast ratio of 100000:1 or higher) was compared with that displayed on a 3.5-inch flat liquid crystal display (with a definition of 326 ppi and a contrast ratio of 800:1) in terms of focal length. Note that each viewer responded in sensitivity evaluation carried out in advance that a stereoscopic effect that he/she felt in a two-dimensional image displayed on the organic EL display was stronger than that displayed on the liquid crystal display. Although the viewers saw the same moving image, the amount of change in focal length in the case of the organic EL display which provided a stronger stereoscopic effect was larger than in the case of the liquid crystal display. This indicates there is a possibility that the intensity of stereoscopic effect that a viewer feels in a two-dimensional image can be evaluated in terms of focal length.

In view of the above, the relationship between the contrast of an image and a stereoscopic effect that a viewer feels was tried to be quantitatively evaluated in this example in such a manner that the amount of physiological response was measured.

As a display device, a 5.9-inch flat organic EL display (with a definition of 249 ppi and a resolution of HD (1280×720×RGB)) was used.

As a light-emitting element, a tandem (stacked-layer) organic EL element emitting white light was used. The light-emitting element has a top-emission structure, where light from the light-emitting element is extracted to the outside of the organic EL display through a color filter.

Two contrast conditions were set as follows. Condition 1 is that the luminance at the time of white display on the entire screen is 200 cd/m$^2$ and that at the time of black display on the entire screen is 0 cd/m$^2$ (measurement limit or less), which are values for utilizing the contrast performance of the organic EL display as it is. Condition 2 is that the luminance at the time of white display on the entire screen is 200 cd/m$^2$ and that at the time of black display on the entire screen is 2 cd/m$^2$. Condition 2 was set for a display whose property of expressing black is poor, like a liquid crystal display. The two conditions were set on the assumption of $\gamma=2.2$. Note that $\gamma$ is a value indicating the response characteristics of the gray scale of an image. The $\gamma$-curve in the case of Condition 2 in a portion corresponding to 0 to 63 gray scale in 256-level gray scale was corrected, and that in the other portion corresponding to 64 to 255 gray scale in 256-level gray scale was the same as that in the case of Condition 1.

The viewers answered in the sensitivity evaluation that they felt a strong stereoscopic effect in a two-dimensional image displayed under Condition 1 in comparison with Condition 2.

For the measurement of the focal length, Binocular Accommodation Auto Ref/Keratometer (WAM-5500, manufactured by REXXAM Co., Ltd.) was used.

The same moving image was displayed as the two-dimensional image in the two contrast conditions. The moving image has been reproduced for 50 seconds. The viewers followed the image in similar ways in the two contrast conditions. The experiment was carried out in a dark room, and the visual distance was 52 cm.

Figure 24:
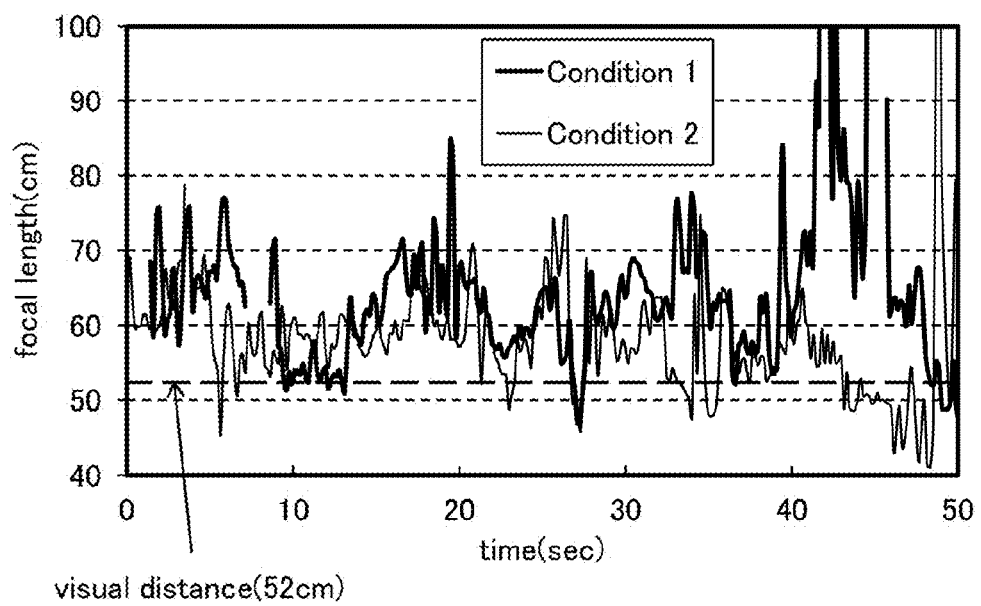
FIG. 24 shows results in Example 2.
Figure 25:
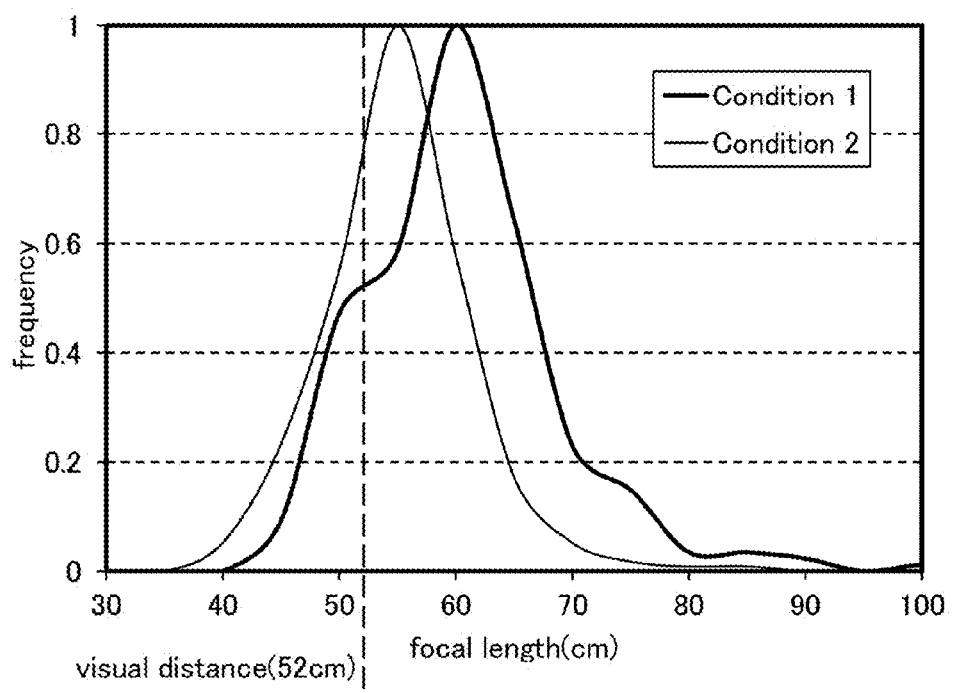
FIG. 25 shows results in Example 2.

FIG. 24 shows the measurement results of the focal length of one viewer. In FIG. 24, the vertical axis represents the focal length of eyes of the viewer, and the horizontal axis represents measurement time. FIG. 25 shows results of plotting the results of FIG. 24, in which the horizontal axis represents the focal length and the vertical axis represents frequency. As seen from FIG. 24 and FIG. 25, a focal point was largely changed in the depth direction in Condition 1 in comparison with Condition 2 although the viewer saw the same moving image. In FIG. 25, the curve in the case of Condition 1 has two peaks, whereas the curve in the case of Condition 2 has one peak. From the above, the viewer was supposed to perceive the front side and the back side under Condition 1.

It is found that when a display has an excellent property of expressing black, a viewer can feel a stronger stereoscopic effect and the amount of a change in focal length becomes larger. The above results suggested that the intensity of stereoscopic effect that the viewer felt in a two-dimensional image can be quantitatively evaluated and analyzed through the measurement of the amount of a change in the focal length of the eyes of the viewer.

This application is based on Japanese Patent Application serial no. 2014-242112 filed with Japan Patent Office on Nov. 28, 2014, and Japanese Patent Application serial no. 2014-249194 filed with Japan Patent Office on Dec. 9, 2014, the entire contents of which are hereby incorporated by reference.

What is claimed is:

1. A display system comprising:
    a display portion;
    a detection portion; and
    a control portion,
    wherein the display portion is flexible,
    wherein the detection portion is configured to detect a condition of a viewer's eye to obtain detection information and to supply the detection information to the control portion, and
    wherein the control portion is configured to extract information on the viewer's fatigue from the detection information and to change a degree of bending of the display portion on the basis of the information on the viewer's fatigue.

2. An electronic device comprising:
    the display system according to claim 1; and
    at least one of an antenna, a battery, a housing, a speaker, a microphone, an operation switch, and an operation button.

3. The display system according to claim 1,
    wherein the detection portion includes a camera.

4. The display system according to claim 1,
wherein the detection portion includes a light source for emitting infrared light and a light-receiving portion for detecting the infrared light reflected from a viewer's eyeball.

5. The display system according to claim 1,
wherein a definition of the display portion is greater than or equal to 220 ppi and less than or equal to 2000 ppi.

6. The display system according to claim 1,
wherein a contrast ratio of the display portion is 1000:1 or higher.

7. The display system according to claim 1,
wherein the control portion uses information comprising a length of screen gazing time and the number of times of blinking per unit time of the viewer when extracting the information on the viewer's fatigue.

8. The display system according to claim 1,
wherein curvature of the display portion is made smaller when the viewer's fatigue is severe.

9. The display system according claim 1,
wherein the control portion comprises a memory, an arithmetic portion and a drive control portion.

10. The display system according to claim 1,
wherein the detection information includes a movement of an eyeball, color or shape of a white of the viewer's eye, an iris, or a pupil, or a movement of an eyelid.

11. A display system comprising:
a display portion;
a detection portion including a camera; and
a control portion,
wherein the display portion is flexible,
wherein the detection portion is configured to detect a condition of a viewer's eye to obtain detection information and to supply the detection information to the control portion, and
wherein the control portion is configured to extract information on the viewer's fatigue from the detection information and to change a degree bending of the display portion on the basis of the information on the viewer's fatigue.

12. An electronic device comprising:
the display system according to claim 11; and
at least one of an antenna, a battery, a housing, a speaker, a microphone, an operation switch, and an operation button.

13. The display system according to claim 11,
wherein the detection portion includes a light source for emitting infrared light and a light-receiving portion for detecting the infrared light reflected from a viewer's eyeball.

14. The display system according to claim 11,
wherein a definition of the display portion is greater than or equal to 220 ppi and less than or equal to 2000 ppi.

15. The display system according to claim 11,
wherein a contrast ratio of the display portion is 1000:1 or higher.

16. The display system according to claim 11,
wherein the control portion uses information comprising a length of screen gazing time and the number of times of blinking per unit time of the viewer when extracting the information on the viewer's fatigue.

17. The display system according to claim 11,
wherein curvature of the display portion is made smaller when the viewer's fatigue is severe.

18. The display system according claim 11,
wherein the control portion comprises a memory, an arithmetic portion and a drive control portion.

19. The display system according to claim 11,
wherein the detection information includes color or shape of a white of the viewer's eye, an iris, or a pupil, or a movement of an eyelid.

* * * * *